United States Patent
Vaya et al.

(10) Patent No.: US 7,985,422 B2
(45) Date of Patent: Jul. 26, 2011

(54) DOSAGE FORM

(75) Inventors: Navin Vaya, Gujarat (IN); Rajesh Singh Karan, Gujarat (IN); Sunil Sadanand Nadkarni, Gujarat (IN); Vinod Kumar Gupta, Gujarat (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 494 days.

(21) Appl. No.: 10/630,446

(22) Filed: Jul. 29, 2003

(65) Prior Publication Data

US 2004/0096499 A1 May 20, 2004

(30) Foreign Application Priority Data

Aug. 5, 2002 (IN) ............................ 697/MUM/2002
Aug. 5, 2002 (IN) ............................ 699/MUM/2002
Jan. 22, 2003 (IN) ............................. 80/MUM/2003
Jan. 22, 2003 (IN) ............................. 82/MUM/2003

(51) Int. Cl.
*A61K 9/26* (2006.01)
*A61K 9/20* (2006.01)

(52) U.S. Cl. ......... 424/469; 424/464; 424/465; 424/468

(58) Field of Classification Search .................. None
See application file for complete search history.

(56) References Cited

U.S. PATENT DOCUMENTS

| | | | | |
|---|---|---|---|---|
| 3,048,526 | A | * | 8/1962 | Boswell ..................... 424/472 |
| 3,336,200 | A | | 8/1967 | Krause et al. |
| 4,139,589 | A | * | 2/1979 | Beringer et al. ............. 264/250 |
| 4,503,031 | A | * | 3/1985 | Glassman .................... 424/467 |
| 4,996,061 | A | * | 2/1991 | Webb et al. ................. 424/475 |
| 5,445,829 | A | * | 8/1995 | Paradissis et al. ........... 424/480 |
| 5,738,874 | A | * | 4/1998 | Conte et al. ................. 424/472 |
| 5,840,332 | A | * | 11/1998 | Lerner et al. ............... 424/464 |
| 5,985,843 | A | | 11/1999 | Higo et al. |
| 6,001,391 | A | | 12/1999 | Zeidler et al. |
| 6,238,699 | B1 | | 5/2001 | Rubin |
| 6,372,254 | B1 | | 4/2002 | Ting et al. |
| 6,475,521 | B1 | * | 11/2002 | Timmins et al. ............ 424/469 |
| 6,660,300 | B1 | * | 12/2003 | Timmins et al. ............ 424/469 |
| 2004/0156902 | A1 | * | 8/2004 | Lee et al. .................... 424/473 |

FOREIGN PATENT DOCUMENTS

WO    WO/01/72286    10/2001

* cited by examiner

*Primary Examiner* — Anand Desai
*Assistant Examiner* — Melissa S Mercier
(74) *Attorney, Agent, or Firm* — Hedman & Costigan, P.C.; James V. Costigan

(57) ABSTRACT

A dosage form comprising of a high dose, high solubility active ingredient as modified release and a low dose active ingredient as immediate release where the weight ratio of immediate release active ingredient and modified release active ingredient is from 1:10 to 1:15000 and the weight of modified release active ingredient per unit is from 500 mg to 1500 mg; a process for preparing the dosage form.

21 Claims, 10 Drawing Sheets

4

DOSAGE FORM

This application claims the priority of Indian applications Serial Nos. 699/MUM/2002, filed Aug. 5, 2002; 697/MUM/2002, filed Aug. 5, 2002; 82/MUM/2003, filed Jan. 22, 2003; and 80/MUM/2003, filed Jan. 22, 2003.

FIELD OF INVENTION

This invention relates to a dosage form comprising of a high dose, high solubility active ingredient as modified release and a low dose active ingredient as immediate release where the weight ratio of immediate release active ingredient and modified release active ingredient is from 1:10 to 1:15000 and the weight of modified release high dose high solubility active ingredient per unit is from 500 mg to 1500 mg and the weight of immediate release active ingredient is up to 50 mg; a process for preparing the formulation.

BACKGROUND OF THE INVENTION

Combining two active ingredients in one pharmaceutical unit to improve patient compliance is known in literature. It can be either in the form of two or more active ingredients in immediate release form or a combination of immediate release and modified release form. There are various techniques by which the combination of immediate release and modified release is formulated in single dosage form.

Several examples of formulations having combination of immediate release active ingredient and modified release active ingredient are described below.

Shoichi Higo and Kazuo Igusa describes in U.S. Pat. No. 5,985,843 various types of pharmaceutical formulations, which consists of a delayed release of sucralfate and an immediate release fraction of another active ingredient. The pharmaceutical dosage forms are a tablet formulation containing immediate release and delayed release granules; a two or three layer tablet; a tablet with delayed release core surrounded by immediate release shell; a delayed release tablet/granule coated with a film of immediate release active ingredient.

Similarly Jurgen Zeidler et.al describes in U.S. Pat. No. 6,001,391 a process for producing solid combination tablets, which have at least two phases. The one of the two phases is processed by melt extrusion technique and contains a water soluble or swellable binder.

A compressed V-shaped center scored double layer tablet is disclosed by George M. Krause et. al in U.S. Pat. No. 3,336,200, one layer of which contains immediate release Active Ingredient and the other layer contains sustained release Active Ingredient. The tablet is divisible in two equal halves. Similarly Jacob A. Glassman described in U.S. Pat. No. 4,503,031 a super fast starting, slow release medicinal tablet, wherein the tablet is comprised of two layers of compressed matrix that are fused together by means of readily dissolvable adhesive substance.

Allan A. Rubin describes in U.S. Pat. No. 6,238,699 B1 a pharmaceutical dosage form of carbidopa and levodopa where both the Active Ingredients are present as immediate release and sustained release. The formulation is in the form of inlay tablet or bilayered tablet or a capsule containing pellets.

Block Jurgen et. al. describes in PCT application No. WO 01/72286 A1 a formulation of vitamin composition whereas a beadlet comprises a slow release core coated by a controlled release coating. The sustained release core is coated with an immediate release layer.

Richard Ting and Charles Hscao describes in U.S. Pat. No. 6,372,254 B1 a press coated, pulsatile active ingredient delivery system which comprises a core of immediate release, enveloped by an extended release compartment.

The need to use active ingredients with different and complementary mechanisms of action frequently arises in treatment of diabetes. There are several reasons to do this, namely, the disease itself is progressive, with deterioration of glycemic control over time; mono-therapeutic attempts to achieve and maintain glycemic control often fail in the long run; multiple defects in the disease and consequently primary drug failures (1,2,3).

Current guidelines for combination therapy advise the use of agents with differing and complementary mechanisms of action in order to maximize therapeutic activity and reduce toxicity. Earlier introduction of combination therapy is increasingly being recommended. The commonly combined active ingredients include biguanides (metformin)+sulphonylureas, biguanides+PPARγ agonists(thiazolidinediones), sulphonylureas+thiazolidinediones, non-sulfonylurea secretagogues (repaglinide)+biguanides etc.

Fixed dose combinations of many of the above mentioned co-administer active ingredients have also been approved by the FDA. Most of these combinations are conventional formulations combined together into a single tablet. However, because of the disparity in the duration of action (half-life), these combinations are given twice or thrice a day.

To reduce this disparity in the duration of action, a novel strategy would be to combine a sustained release formulation of one active ingredient (shorter duration of action) with conventional formulation (long duration of action) of another active ingredient. This would make it possible to give the active ingredients in same dosing frequency.

This type of combination will give better compliance and a relative freedom from mealtime drug administration, thus, improving the quality of life. More importantly, because of prolonged duration of action, it shall produce a stricter control of blood glucose and consequently less diabetic complications.

The techniques described above do not work well when the difference in the dose of active ingredients are high for example where the weight ratio of active ingredients in immediate release and modified release is from 1:10 to 1:15000 and the dose of modified release active ingredient per unit is from 500 mg to 1500 mg. The techniques described in the prior art do not give good results when the active ingredient is highly soluble. The weight of the dosage form becomes very high, or complicated process for manufacturing is required, or accurate dosing of low dose active ingredient is difficult when the techniques reported in the prior art are utilized to make formulation with high dose, high solubility active ingredient in the form of modified release and small dose active ingredient into immediate release form where the weight ratio of immediate release active ingredient and modified release active ingredient is from 1:10 to 1:15000 and the weight of modified release active ingredient per unit is from 500 mg to 1500 mg and also it is inconvenient to swallow due to large size.

Accordingly a need exists for a dosage form providing combination of immediate release and modified release active ingredients and providing solution to problems associated with dosage forms described in prior art. Further, the dosage form should be simple and economical to produce.

Therefore an object of the present invention is a dosage form of combination of a high dose, high solubility active ingredient as modified release and a low dose active ingredient as immediate release where the weight ratio of immediate release active ingredient and modified release active ingredient is from 1:10 to 1:15000 and the weight of modified release active ingredient per unit is from 500 mg to 1500 mg.

Another object of the present invention is a dosage form, which is suitable for swallowing for humans containing two active ingredients one of which is in modified release form and other in immediate release form.

Accordingly, an object of the present invention to provide a dosage form, which uses dual retard technique to control the release of the high dose, high solubility active ingredient and significantly reduce the amount of release controlling agents which are otherwise required in very high quantity and make the dosage form very bulky and therefore pose difficulty in swallowing.

A further object of the present invention is to provide a dosage form, containing one active ingredient in an immediate release form and another active ingredient as modified release and the release or disintegration of the immediate release active ingredient is not hindered by the modified release ingredient.

Another object of the present invention is to provide a dosage form, which effectively avoids the problem of separation of layers of multilayered tablets.

A further object of the present invention is a formulation, which gives accurate dosing and is prepared by conventional and simple processes.

A further object of the present invention is to provide a dosage form, which can be given twice a day or more preferably can be given once a day.

SUMMARY OF THE INVENTION

The above objects are realized by a dosage form, which is comprised of an inner portion and an outer portion. The inner portion is surrounded by the outer portion in such a manner that only one surface of the inner portion is exposed. The inner portion contains a low dose active ingredient in immediate release form and the outer portion contains a high dose, high solubility active ingredient as modified release. The weight of the immediate release low dose active ingredient and high dose, high solubility modified release active ingredient is from 1:10 to 1:15000 and the weight of modified release active ingredient per unit is from 500 mg to 1500 mg.

The present invention also provides solid oral dosage form comprising a composition according to the invention.

The present invention also teaches the use of dual retard technique to effectively control the release rate of modified release active ingredient by using small quantity of release controlling agents. This dual retard technique thus sufficiently reduces the size of the dosage form, which is convenient for swallowing.

The present invention further teaches the use of hydrophobic release controlling agents, which do not hinder the release of the immediate release active ingredient.

The present invention further provides the dosage form that effectively prevents the problem of separation of the layers of the multilayered tablets.

The present invention also provides a novel process for preparing the novel formulations of the invention.

The present invention further provides a method of treating an animal, particularly a human in need of treatment utilizing the active agents, comprising administering a therapeutically effective amount of composition or solid oral dosage form according to the invention to provide administration of two active ingredients one in immediate release and other in modified release form.

DETAILED DESCRIPTION OF THE INVENTION

This invention relates to a novel dosage form of combination of high dose high solubility active ingredient, as modified release and low dose active ingredient as immediate release, suitable for swallowing comprising dual retard technique to control the release of the high dose high solubility active ingredient, with sufficient reduction in the amount of release controlling agent, without interfering the release of each other.

The term "modified release" as used herein in relation to the composition according to the invention or a rate controlling polymer or used in any other context means release, which is not immediate release and is taken to encompass controlled release, sustained release, prolonged release, timed release, retarded release, extended release and delayed release. The term "modified release dosage form" as used herein can be described as dosage forms whose drug-release characteristics of time course and/or location are chosen to accomplish therapeutic or convenience objectives not offered by conventional dosage forms such as a solution or an immediate release dosage form. Modified release solid oral dosage forms include both delayed and extended release drug products (as per US FDA guideline for 'SUPAC-MR: Modified Release Solid Oral Dosage Forms').

The term "immediate release" as used herein in relation to composition according to the invention or used in any other context means release which is not modified release and releases more than 70% of the active ingredient within 60 minutes. The term "immediate release dosage form" as used herein can be described as dosage form which allows the drug to dissolve in the gastrointestinal contents, with no intention of delaying or prolonging the dissolution or absorption of the drug (as per US FDA guideline for 'SUPAC-MR: Modified Release Solid Oral Dosage Forms').

The term "dosage form" denotes any form of the formulation that contains an amount sufficient to achieve a therapeutic effect with a single administration.

The term "active ingredient" refers to an agent, active ingredient compound or other substance, or compositions and mixture thereof that provide some pharmacological, often beneficial, effect. Reference to a specific active ingredient shall include where appropriate the active ingredient and it's pharmaceutically acceptable salts.

The term "high dose" as used herein refers to the weight of active ingredient in unit dosage form according to the invention is from 500 mg to 1500 mg.

The term "low dose" as used herein refers to the weight of the active ingredient in unit dosage form according to the invention is less than or equal to 50 mg.

The term "high solubility" as used herein in relation to high dose active ingredient means that from less than 1 part to 30 parts of the water will require dissolving 1 part of active ingredient.

The invention provides a novel dosage form of high dose, high solubility active ingredient as modified release and a low dose active ingredient as immediate release where the weight ratio of immediate release active ingredient and modified release active ingredient is from 1:10 to 1:15000 and the weight of modified release antidiabetic active ingredient per unit is from 500 mg to 1500 mg; a process for preparing the dosage form.

The dosage form comprises of two parts (i) inner portion as an immediate release and (ii) outer portion as modified release. The two parts are compressed together in such a way that one surface of the inner portion remains exposed and the remaining surfaces are covered by the outer portion.

(i) Inner portion—Inner portion comprises of a low dose active ingredient and includes one or more commonly used excipients in oral immediate release pharmaceutical formulations.

The low dose active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, the low dose active ingredient, where applicable, may be present either in the form of one substantially optically pure enantiomer or as a mixture of enantiomers or polymorphs thereof.

In the dosage form of the present invention, the inner portion may optionally contain more than one low dose active ingredient.

In the dosage form of the present invention, the inner portion may optionally contain more than one low dose antidiabetic active ingredient.

The low dose active ingredient is in the form of immediate release and has dose of 50 mg or less.

The low dose active ingredients are comprises of the following therapeutic classes but not limited to antidiabetic agents, anti-histamines, anti-depressants, anti-viral agents, anesthetics, antacids, anti-arththriics, antibiotics, anti-psychotics, anti-spasmodics, anxiolytic agents, appetite suppressants, cardiovascular agents, cough suppressants, emollients, gastro-intestinal agents, growth regulators, respiratory stimulants, vitamins, angiotensin converting enzyme inhibitors, anti-asthmatics, anti-cholesterolemics, anti-convulsants, anti-depressants, anti-diarrhea preparations, anti-infective, anti-inflammatory agents, anti-nauseants, anti-stroke agents, anti-tumor drugs, anti-tussives, anti-uricemic drugs, amino-acid preparations, antiemetics, antiobesity drugs, antiparasitics, antipyretics, appetite stimulants, celebral dilators, chelating agents, cholecystokinin antagonists, cognition activators, deodorants, dermatological agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors, vertigo agents, sulphonylurease, meglitinides, PPAR gama agonist [insulin sensitisers (thiazolidinedione)], PPAR alpha and gamma agonist, alpha-glucosidase inhibitors and the active ingredients described in U.S. Pat. Nos. 2,968, 158, 3,097,242, 3,454,635, 3,654,357, 3,668,215, 3,669,966, 3,708,486, 3,801,495, 5,104,888, 5,232,945, 5,264,451, 5,478,852, 6,296,874, and European patent publication numbers EP0008203, EP0032128, EP0139421, EP0155845, EP0177353, EP0208420, EP0257881, EP0306228, EP0319189, EP0332331, EP0332332, EP0428312, EP0489663, EP0508740, EP0528734, EP0533933, EP0833933, EP87112480.6 and Japanese patent number 05271204 and United Kingdom patent numbers 5504078, GB2088365A and PCT patent application numbers WO91/19702, WO92/03425, WO92/18501, WO93/02079, WO93/21166, WO93/22445, WO94/01420, WO94/05659.

Examples of low dose active ingredients comprises of but not limited to zafirlukast, quinapril hydrochloride, isotretinoin, rabeprazole sodium, estradiol(e2), norethindrone acetate, risedronate sodium, pioglitazone HCl, amphetamine, anagrelide hydrochloride, biperiden HCl, mephalan, alprazolam, ramipril, naratriptan hydrochloride, leflunomide, anastrozole, exemestane, paroxetine mesylate, candesartan cilexetil, almotriptan, cerivastatin, betaxolol hydrochloride, bisoprolol fumarate, deloratadine, clonazepam, clorazepate dipotassium, clozapine, methylphenidate HCl, carvedilol, warfarin sodium, norgestrel, ethinyl estradiol, cyclophosphamide, pemoline, liothyronine sodium, misoprostol, tolterodine tartrate, dextroamphetamine sulfate, dicyclomine hydrochloride, digoxin, oxybutynin chloride, doxazosin mesylate, ethacrynate sodium, venlafaxine HCl, enalapril maleate, estradiol, estropipate, famotidine, letrozole, fludrocortisone acetate, fluoxetine, dexmethylphenidate hci, alendronate sodium, ziprasidone, glipizide, glyburide, miglitol, guanabenz acetate, haloperidol, doxercalciferol, zalcitabine, hydrochlorothiazide, hydromorphone HCl, indapamide, estradiol, nitric oxide, ketorolac tromethamine, clonazepam, granisetron, lamotrigine, fluvastatin sodium, levonorgestrel, levothyroxine sodium, atorvastatin calcium, lisinopril, minoxidil, loperamide, loratidine, lorazepam, lovastatin, pravastatin sodium, fluvoxamine maleate, acetaminophen, acyclovir, aminocaproic acid, pitavastatin, rosuvastatin, dalvastatin, sertraline, pitavastatin, rosuvastatin, dalvastatin, escetalopr am, sertraline, celecoxib, parecoxib, valdecoxib, glibenclamide (glyburide), glipizide, gliclazide, glimepiride, tolazamide, tolbutamide, clorpropamide, gliquidone, nateglinide, glyburide, glisoxepid, glibornuride, phenbutamide, tolcyclamide, repaglinide, troglitazone, ciglitazone, pioglitazone, englitazone, acarbose, voglibose, emiglitate, miglitol, farglitazar, (S)-2-ethoxy-3-[4-(2-{4-methanesulfonyloxyphenyl}ethoxy)phenyl]propanoic acid, 3-{4-[2-(4-tert-butoxycarbonylaminophenyl)ethoxy]phenyl}-(S)-2-ethoxy propanoic acid and L-6766892.

Further examples of low dose, antidiabetic active ingredients comprises of but not limited to JTT-501 (PNU-182716) (Reglitazar), AR-H039242, MCC-555 (Netoglitazone), AR-H049020, Tesaglitazar), CS-011 (CI-1037), GW-409544X, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336 and EML-16257.

As indicated above the inner portion of the present invention may comprise auxiliary excipients such as for example diluents, binders, lubricants, surfactants, disintegrants, plasticisers, anti-tack agents, opacifying agents, pigments, and such like. As will be appreciated by those skilled in the art, the exact choice of excipient and their relative amounts will depend to some extent on the final oral dosage form.

Suitable diluents include for example pharmaceutically acceptable inert fillers such as microcrystalline cellulose, lactose, starch, dibasic calcium phosphate, saccharides, and/or mixtures of the foregoing. Examples of diluents include microcrystalline celluloses such as those sold under the Trade Mark Avicel PH 101, Avicel PH 102, Avicel PH 112, Avicel PH 200, Avicel PH301 and Avicel PH 302; lactose such as lactose monohydrate, lactose anhydrous and Pharmatose DCL21 (Pharmatose is a Trade Mark), including anhydrous, monohydrate and spray dried forms; dibasic calcium phosphate such as Emcompress (Emcompress is a Trade Mark); mannitol; Pearlitol SD 200 (Pearlitol SD 200 is a trade mark); starch; sorbitol; sucrose; and glucose.

Suitable binders include for example starch, povidone, hydroxypropylmethylcellulose, pregelatinised starch, hydroxypropylcellulose and/or mixtures of the foregoing.

Suitable lubricants, including agents that act on the flowability of the powder to be compressed are, for example, colloidal slilcon dioxide such as Aerosil 200 (Aerosil is a Trade Mark); talc; stearic acid, magnesium stearate, calcium stearate and sodium stearyl fumarate.

Suitable disintegrants include for example lightly crosslinked polyvinyl pyrrolidone, corn starch, potato starch, maize starch and modified starches, croscarmellose sodium, cross-povidone, sodium starch glycolate and combinations and mixtures thereof.

(ii) Outer Portion: The outer portion comprises of a) Micro matrix particles containing high dose, high solubility active ingredient and one or more hydrophobic release controlling agent, b) Coating of Micro matrix particles with one or more hydrophobic release controlling agents. The outer portion may also include one or more commonly used excipients in oral pharmaceutical formulations. The release of the high dose, high solubility active ingredient is controlled through dual retard technique. The dual retard technique is a combination of matrix formulations and reservoir formulations. First the micro matrix particles of high dose, high solubility dose active ingredient and one or more hydrophobic release controlling agents are formed and then these are further coated with one or more release controlling agents. Thus the dual retard release technique presents the double barriers and effectively controls the diffusion of the high dose, high solubility active ingredients from the present invention in predictable manner and also significantly reduces the amount of release controlling agents which are otherwise required in very high quantity and make the dosage form very bulky and therefore pose difficulty in swallowing. The other advantages of the present invention are such as it reduces the chances of dose dumping, unnecessary burst effects and failure of the system, which are otherwise usually associated with simple matrix or reservoir systems.

Further advantages of present invention include the disintegration of inner portion is not hindered as nonswellable release controlling agents are used which do not swell and maintain the shape during operation and it effectively prevents the separation of the layers of the multilayered tablets which is normally associated with normal multilayered tablets.

The high dose, high solubility active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, the high dose, high solubility active ingredient, where applicable, may be present either in the form of one substantially optically pure enantiomer or as a mixture of enantiomers or polymorphs thereof.

The high dose, high solubility active ingredient is in the form of modified release and has dose from 500 mg to 1500 mg.

The high dose, high solubility active ingredients are comprises of the following therapeutic classes but not limited to antidiabetic agents, anti-histamines, anti-depressants, anti-viral agents, anesthetics, antacids, anti-arthritis, antibiotics, anti-psychotics, anti-spasmodics, anxiolytic agents, appetite suppressants, cardiovascular agents, cough suppressants, emollients, gastro-intestinal agents, growth regulators, respiratory stimulants, vitamins, angiotensin converting enzyme inhibitors, anti-asthmatics, anti-cholesterolemics, anti-convulsants, anti-depressants, anti-diarrhea preparations, anti-infective, anti-inflammatory agents, anti-nauseants, anti-stroke agents, anti-tumor drugs, anti-tussives, anti-uricemic drugs, amino-acid preparations, antiemetics, antiobesity drugs, antiparasitics, antipyretics, appetite stimulants, cerebral dilators, chelating agents, cholecystokinin antagonists, cognition activators, deodorants, dermatological agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors,vertigo agents, biguanides and the active ingredients described in U.S. Pat. Nos. 3,957,853, 4,080,472, 3,174,901, 4,835,184, 6,031,004.

Examples of high dose, high solubility active ingredients comprises of but not limited to potassium chloride, metformin hydrochloride, phenformin, buformin, clindamycin, hydroxyurea, erythromycin, lactobionate, vancomycin hydrochloride, balsalazide disodium, sodium valproate, niacin, aminocaproic acid, acetaminophen, Ciprofloxacin, quetiapine. Other drugs suitable for use and meeting the solubility and dose criteria described above will be apparent to those skilled in the art.

In the dosage form of the present invention, the outer portion may optionally contain more than one high dose high solubility active ingredient.

In the dosage form of the present invention, the outer portion may optionally contain more than one high dose high solubility antidiabetic active ingredient.

As indicated above the outer portion of the present invention may comprise auxiliary excipients such as for example lubricants, plasticisers, anti-tack agents, opacifying agents, pigments, and such like. As will be appreciated by those skilled in the art, the exact choice of excipient and their relative amounts will depend to some extent on the final oral dosage form.

Suitable lubricants, including agents that act on the flowability of the powder to be compressed are, for example, colloidal silicon dioxide such as Aerosil 200 (Aerosil is a Trade Mark); talc; stearic acid, magnesium stearate, calcium stearate and sodium stearyl fumarate.

In micro matrix particles, the active ingredient and one or more hydrophobic release controlling agents are preferably present in a ratio of from 100:1 to 100:75, more particularly from 100:2.5 to 100:50, still more preferably from 100:2.5 to 100:30 and most preferably from 100:2.5 to 100:20.

In outer portion, micro matrix particles and coating of one or more hydrophobic release controlling agents are preferably present in a ratio of from 100:0.5 to 100:75, more particularly from 100:2.5 to 100:50, still more preferably from 100:2.5 to 100:30 and most preferably from 100:2.5 to 100:20.

According to one embodiment the release controlling agents are pharmaceutically excipients, which are hydrophobic in nature.

The polymers that can be used to form the rate-controlling membrane or micromatrix are described in greater detail herein below.

The hydrophobic release controlling agents are selected from but are not limited to Ammonio methacrylate copolymers type A and B as described in USP, methacrylic acid copolymer type A, B and C as described in USP, Polyacrylate dispersion 30% as described in Ph. Eur., Polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly (hexyl methacrylate). Poly(isodecyl methacrylate), poly (lauryl methacrylate), poly (phenyl methacrylate), poly (methyl acrylate), poly (isopropyl acrylate), poly (isobutyl actylate), poly (octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glycerol distearate; glycerol monooleate, acetylated monoglycerides, tristearin, tripalmitin, cetyl esters wax, glyceryl palmitostearate, glyceryl behenate, and hydrogenated castor oil.

The ammonio methacrylate co-polymers are preferably selected from the group consisting of poly(ethyl acrylate, methyl methacrylate, trimethylammonioethyl methacrylate chloride) 1:2:0.1; poly(ethyl acrylate, methyl methacrylate, trimethylamonioethyl methacrylate chloride) 1:2:0.2 and poly (ethyl acrylate, methyl methacrylate) 1:1.

According to an especially preferred embodiment the release controlling agents contains ammonio methacrylate co-polymers and fatty acid esters as hereinafter described.

The suitable hydrophobic agents are polymers sold under the Trade Mark Eudragit RS (Ammonio Methacrylate Copolymer type B USP), Eudragit NE 30D (Polyacrylate dispersion 30% Ph. Eur.), Eudragit RL (Ammonio Methacrylate Copolymer type A USP) and Kollicoat SR 30 D and fatty acid esters such as glyceryl behenate, glycerol distearate and hydrogenated castor oil. Eudragit polymers are polymeric lacquer substances based on acrylate and/or methacrylates.

The outer portion can also include one or more commonly used excipients in oral pharmaceutical formulations.

Representative commonly used excipients in oral pharmaceutical formulations include talc, fumed silica, glyceryl monostearate, magnesium stearate, calcium stearate, kaolin, colloidal silica, gypsum, Tween 80, Geleol pastiles (trade mark), micronised silica and magnesium trisilicate.

The quantity of commonly used excipients in oral pharmaceutical formulations used is from about 0.5% to about 200% by weight, preferably from 2 to 100% more particularly 10 to 60% based on the total dry weight of the polymer.

The outer portion can also include a material that improves the processing of the release controlling agents. Such materials are generally referred to as "plasticisers" and include, for example, adipates, azelates, benzoates, citrates, isoebucaes, phthalates, sebacates, stearates, tartrates, polyhydric alcohols and glycols.

Representative plasticisers include acetylated monoglycerides; butyl phthalyl butyl gylcolate; dibutyl tartrate; diethyl phthalate; dimethyl phthalate,; ethyl phthalyl ethyl glycolate; glycerin; ethylene glycol, propylene glycol; Triethyl citrate; triacetin; tripropinoin; diacetin; dibutyl phthalate; acetyl monoglyceride; polyethylene glycols; castor oil; triethyl citrate; polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylexyl phthalate, di-n-octyl phthalate, di-I-octyl phthalate, di-I-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate and glyceryl monocaprate.

The amount of plasticiser to be used is from about 1% to 50% based on the weight of the dry release controlling agent(s).

The amount of release controlling agent(s) to be used in forming the outer portion will be determined based on various parameters such as the desired delivery properties, including the amount of active ingredient to be delivered, the active ingredient release rate desired, and the size of the micro matrix particles.

The novel dosage form of the present invention can be manufactured by the following procedure:

A) Inner Portion

The granules of the inner portion can be manufactured in accordance with usual techniques in which the active ingredient and other excipients are mixed and granulated by adding solution of binder in a low or high shear mixer or by fluidized bed granulation. The granulate is dried, preferably in a fluidized bed dryer. The dried granulate is sieved and mixed with lubricants and disintegrants. Alternatively the manufacture of granules of inner portion can be made by direct mixing of the directly compressible excipients or by roller compaction.

B) Outer Portion

The micro matrix particles of the outer portion can be manufactured in accordance with usual techniques in which the active ingredient and one or more hydrophobic release controlling agents are mixed and granulated by adding solvent in a low or high shear mixer or by fluidized bed granulator. The granulate is dried, preferably in a fluidized bed dryer. The dried granulate is sized. The sizing of the micromatrix particles can be done using oscillating granulator, comminuting mill or any other conventional method. The sieve used for the sizing can have openings from 0.25 mm to 5 mm. Alternatively the micro matrix particles can be made by extrusion, spheronization or by roller compaction. The micro matrix particles can be coated by a solution of one or more hydrophobic release controlling agents by any known method, including spray application. Spraying can be carried out using a fluidized bed coated (preferably Wurster coating), or in a pan coating system. Alternatively the coating of the micro matrix particles with one or more rate controlling agents can be done by hot melt process using a granulator or fluidized bed coated (preferably Wurster coating), or in a pan coating system.

C) Tablet Compression

The compression of tablets is carried out on usual press coaters (e.g. machines of the Manesty, Cadmach or Kilian) with slight modification. The device such as feed frame and hoppers making top layer are eliminated. The granules of the inner layer are charged in the hopper of the machine compressing first layer and the granules of the outer layer are charged in the hopper of the machine compressing the coating. On operation only the bottom layer of the coating (outer portion) is deposited into the die and the first layer is placed on it. The compression wheels then embed the first layer in the granules of the outer layer, displacing some of latter to form sides, and finally press the whole into the tablet. The resultant tablet has inner portion covered by the outer portion from all the sides except top surface that remains uncovered and the level of the inner portion and the outer portion is same. The tablets can be made of various sizes and shapes. The present invention uses round punch tooling with upper flat bottom punches and lower flat bottom beveled edges lower punches for the compression of inner portion and oblong shaped flat bottom beveled edges punches for the compression of the outer portion.

BRIEF DESCRIPTION OF THE DRAWINGS

Referring to FIGS. 1 to 3, a dosage form 4 as described in the present invention having an inner portion 1 containing low dose active ingredient as immediate release and outer portion 2 containing high dose, high solubility active ingredient as modified-release. FIGS. 4(a) & 4(b) shows the cross section of the coated micro matrix particles 5 and having 6 a high dose, high solubility active ingredient, 7 hydrophobic release controlling agent and 8 a coating of hydrophobic release controlling agent. FIG. 5 shows the release profile of a low dose active ingredient as immediate release 9 and the release profile of a high solubility active ingredient as modified release 10. FIGS. 6 and 7 shows release of high dose, high solubility active agent 11 & 12 and 15 & 16 as per example 1 & 2 respectively from a dosage form prepared using dual retard technique as described in the present invention and release of high dose, high solubility active agent 13 & 14 and 17 & 18 as per example 3 & 4 respectively from a dosage form prepared without using dual retard release technique. The total quantity of the hydrophobic release controlling agent is same in all the dosage forms inspite of that the figures clearly shows that dual retard technology significantly reduces the burst effect and effectively controls the release rate of the high dose, high solubility active ingredient for prolonged period.

DESCRIPTION OF THE PREFERRED EMBODIMENTS

Figure 1:
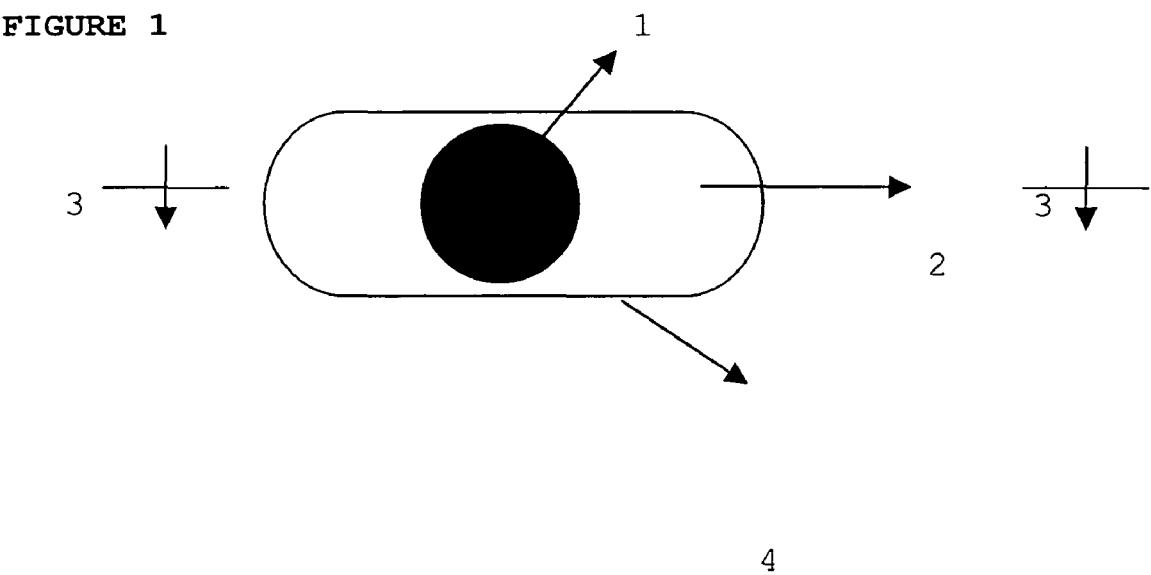
FIG. 1 is a plan view of the dosage form described in the present invention.
Figure 2:
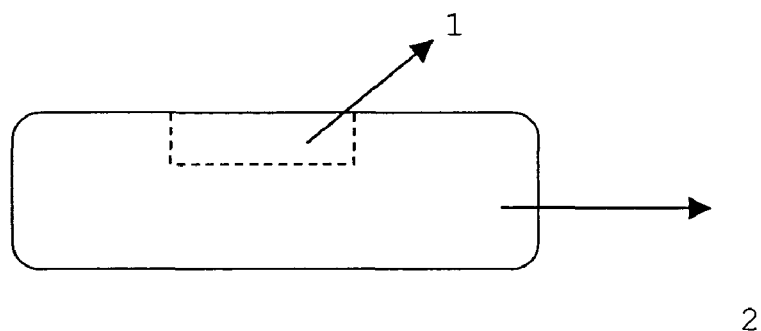
FIG. 2 is an edge view of the dosage form described in the present invention.
Figure 3:
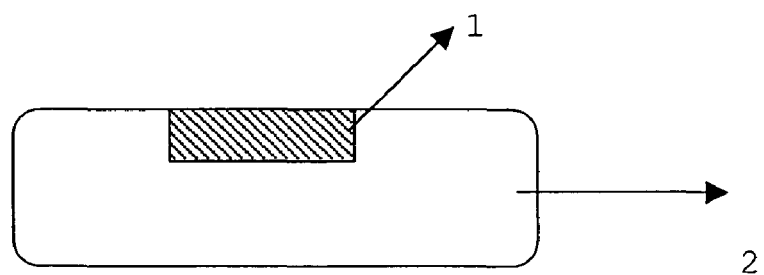
FIG. 3 is a transverse section view as seen along the line 3-3 of FIG. 1.
Figure 4A:
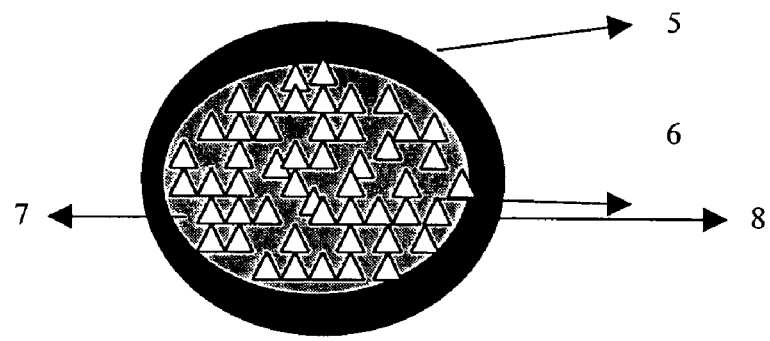
FIG. 4(a) is a cross section of coated micro matrix particles prepared by spheronization and coating for the purpose of illustration only.
Figure 4B:
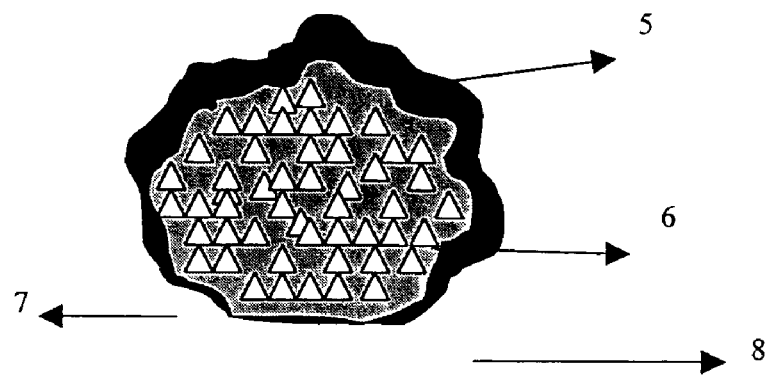
FIG. 4(b) is a cross section of coated micro matrix particles prepared by granulation and coating for the purpose of illustration only.
Figure 5:
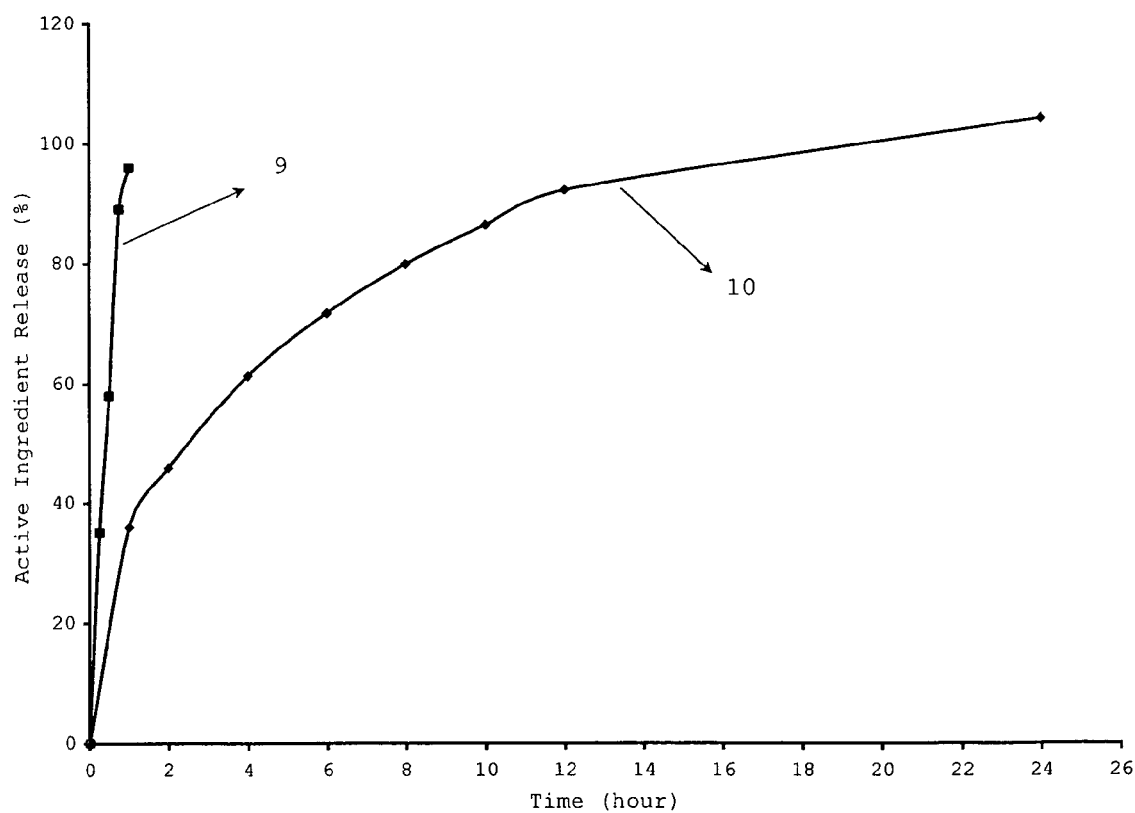
FIG. 5 is a plot of % active ingredient versus time for immediate release and modified release active agent.
Figure 6:
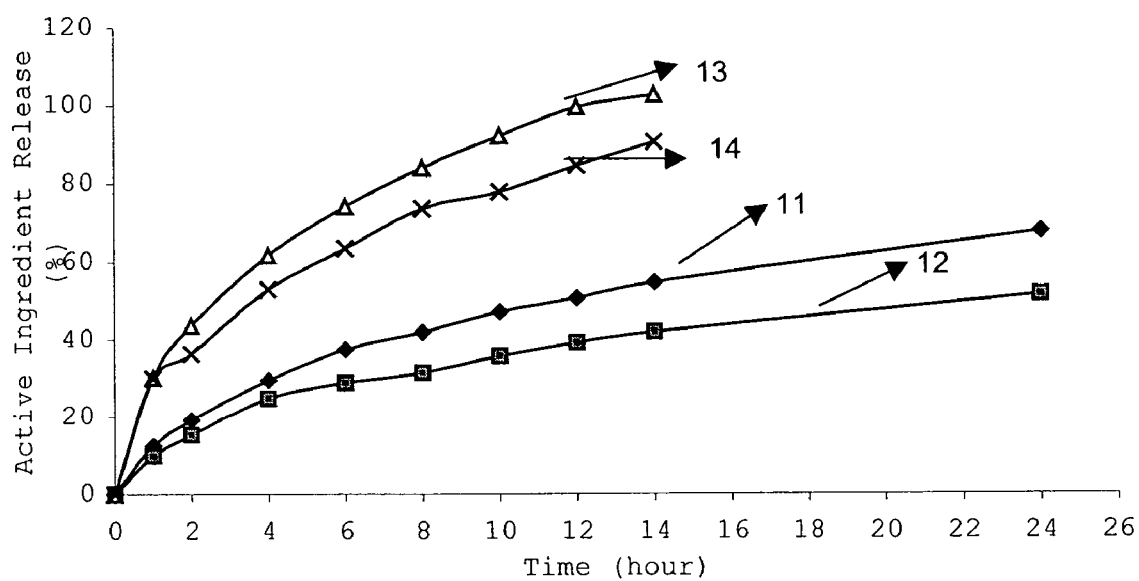
FIG. 6 is a plot of % active ingredient versus time for modified release active agent prepared using dual retard technique as described in the present invention and prepared without retard release technique as per examples 1 and 3.
Figure 7:
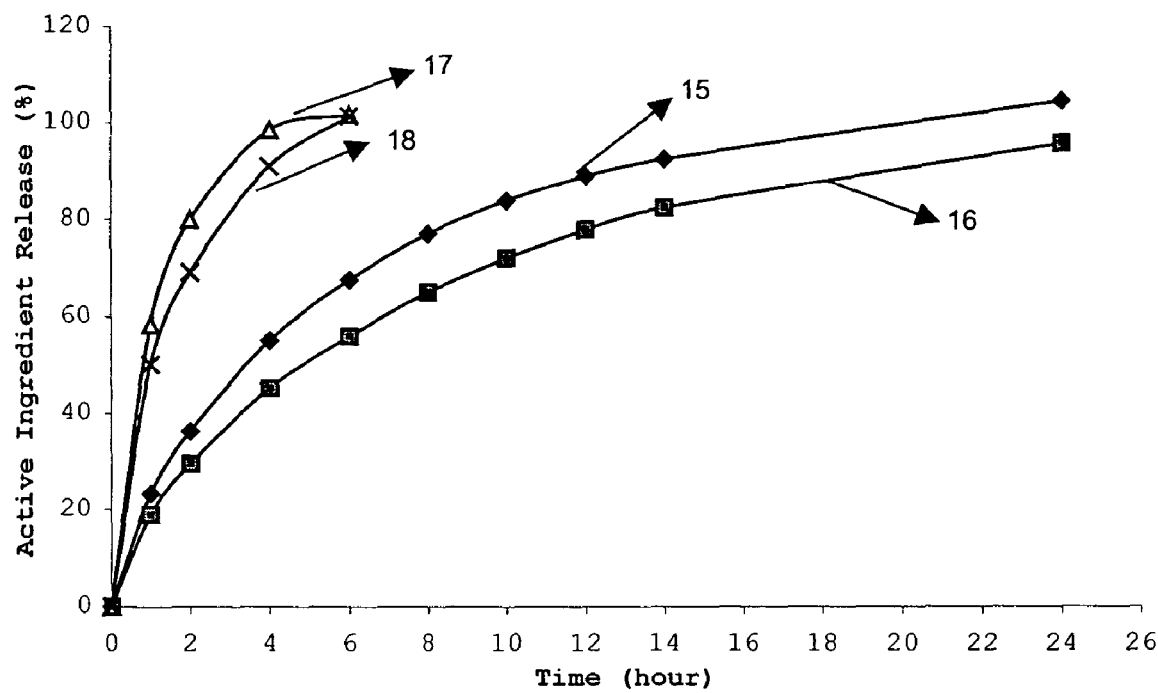
FIG. 7 is a plot of % active ingredient versus time for modified release active agent prepared using dual retard technique as described in the present invention and prepared without retard release technique as per examples 2 and 4.

The following examples further illustrate but by no means limit the present invention.

The dissolution of novel dosage form of the present invention was determined by following method.

For sodium valproate—
  Instrument—Apparatus I, USP (basket)
  Revolution—60/min.
  Temperature—37±0.5° C.
  Dissolution medium—1000 ml pH 6.8 buffer For niacin—
  Instrument—Apparatus I, USP (Basket)
  Revolution—100/min.
  Temperature—37±0.5° C.
  Dissolution medium—900 ml 0.1 N HCl For lamotrigine—
  Instrument—Apparatus II, USP (Paddle)
  Revolution—100/min.
  Temperature—37±0.5° C.
  Dissolution medium—1000 m10.001 N HCl For pravastatin sodium—
  Instrument—Apparatus II, USP (Paddle)
  Revolution—100/min.
  Temperature—37±0.5° C.
  Dissolution medium—900 ml pH 6.8 buffer For metformin hydrochloride—
  Instrument—Apparatus II, USP (Paddle)
  Revolution—50/min.
  Temperature—37±0.5° C.
  Dissolution medium—900 ml 0.1 N HCl For rosiglitazone maleate—
  Instrument—Apparatus II, USP (Paddle)
  Revolution—100/min.
  Temperature—37±0.5° C.
  Dissolution medium—500 ml 0.01 N HCl For glimepiride—
  Instrument—Apparatus II, USP (Paddle)
  Revolution—75/min.
  Temperature—37±0.5° C
  Dissolution medium—500 ml 0.5% sodium lauryl sulfate in water The composition of outer portion in the dosage form comprising high dose high solubility antidiabetic active ingredient is as follows—
  Micro matrix particles—
    Metformin hydrochloride 75% w/w to 99% w/w
    Eudragit RS 1% w/w to 25% w/w
  Coated micro matrix particles
    Micro matrix particles 70% w/w to 99% w/w
    Hydrogenated castor oil 1% w/w to 30% w/w
    Magnesium stearate 0% w/w to 2% w/w The dissolution of high dose high solubility ingredient of the formulation of the present invention is achieved not more than 45% in 1 hour and from 25 to 90% in six hours.

The dissolution of metformin hydrochloride is achieved not more than 50% in 1 hour, and from 30 to 90% is in four hours and not less than 65% in 12 hours.

After oral administration of a dosage form of the present invention the maximum plasma concentration can be achieved between 700 ng/ml and 2500 ng/ml, preferably from 900 ng/ml to 2400 ng/ml and more preferably from 1000 ng/ml to 2350 ng/ml. The invivo mean dissolution time (MDT) of the dosage form of the present invention is 4 to 6 hours. The minimum plasma concentration (at 24 hours) of the said dosage form ranges between 0 to 450 ng/ml after oral administration.

EXAMPLES

Example 1

1) Production of Inner Portion 11.71% w/w of pravastatin sodium is mixed with 52.62% w/w of lactose monohydrate and 22.22% w/w starch and the mixture is granulated in a binder of 2.22 v povidone in water and then dried. The granules are sieved and mixed with 1.11% w/w magnesium stearate, 9.0 g sodium starch glycolate, 0.11% w/w lake of sunset yellow. This mixture is compressed to 90 mg weight tablets having a diameter of 6.35 mm.

2) Production of Outer Portion

A) Micro matrix particles—90.91% w/w of niacin is mixed with 9.09% w/w of Eudragit RSPO (Ammonio Methacrylate Copolymer type B USP) and the mixture is granulated with a solvent mixture of acetone and methylene chloride and then dried. The granules are sized.

B) Coating of Micro matrix particles—85.84% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

3) Compression of Tablets

Tablet (A)—90 mg granules of inner portion are pressed to tablets(equal to 10 mg pravastatin) using 6.35 mm round punches and 643 mg granules of outer portion (equal to 500 mg niacin)are compressed using 14.95×8.35 mm oblong punches.

Tablet (B)—90 mg granules of inner portion are pressed to tablets(equal to 10 mg pravastatin) using 6.35 mm round punches and 1286 mg granules of outer portion (equal to 1000 mg niacin)are compressed using 20.3×9.8 mm oblong punches.

The compression is done on press coater machine in such a manner that the resultant tablet has inner portion covered by the outer portion from all the sides except top surface that remains uncovered and the level of the inner portion and the outer portion is on the same surface.

The dissolution rate of the novel dosage form was determined (Table 1 and 2)

TABLE 1

Dissolution profile of tablet (A)

| Niacin | | Pravastatin sodium | |
| --- | --- | --- | --- |
| Time (hour) | % Released | Time (min) | % Released |
| 1 | 12.4 | 45 | 83.8 |
| 2 | 19.1 | 60 | 84.1 |
| 4 | 29.4 | | |
| 6 | 37.4 | | |
| 8 | 41.9 | | |
| 10 | 47.1 | | |
| 12 | 50.6 | | |
| 14 | 54.6 | | |
| 24 | 67.7 | | |

TABLE 2

Dissolution profile of tablet (B)

| Niacin | | Pravastatin sodium | |
| --- | --- | --- | --- |
| Time (hour) | % Released | Time (min) | % Released |
| 1 | 9.8 | 45 | 84.1 |
| 2 | 15.3 | 60 | 85.6 |
| 4 | 24.7 | | |
| 6 | 28.7 | | |
| 8 | 31.4 | | |
| 10 | 35.7 | | |
| 12 | 39.1 | | |
| 14 | 41.9 | | |
| 24 | 51.5 | | |

Example 2

1) Production of Inner Portion 38.47% w/w of lamotrigine is mixed with 2.71% w/w of crosspovidone and 0.18% w/w colloidal silicon dioxide and the mixture is granulated in a binder of 0.71% w/w povidone in water and then dried. The granules are sieved and mixed with 28.70% w/w of Mannitol (Pearlitol SD 200 R.T.M.), 12.31% w/w of crosspovidone, 2.31% w/w of magnesium stearate, 6.15% w/w aspartame, 2.31% w/w talc, 5.0% w/w flavour and 1.15% w/w of colloidal silicon dioxide. This mixture is compressed to 65 mg weight tablets having a diameter of 5.55 mm.

2) Production of Outer Portion

A) Micro matrix particles—90.91% w/w of sodium valproate is mixed with 9.09% w/w of Eudragit RSPO (Ammonio Methacrylate Copolymer type B USP) and the mixture is granulated with a solvent mixture of acetone and methylene chloride and then dried. The granules are sized.

B) Coating of Micro matrix particles—85.84% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

1) Compression of Tablets

Tablet (A)—65 mg granules of inner portion are pressed to tablets(equal to 25 mg lamotrigine) using 5.55 mm round punches and 643 mg granules of outer portion (equal to 500 mg sodium valproate)are compressed using 14.95×8.35 mm oblong punches.

Tablet (B)—65 mg granules of inner portion are pressed to tablets(equal to 25 mg lamotrigine) using 5.55 mm round punches and 1286 mg granules of outer portion (equal to 1000 mg sodium valproate)are compressed using 20.3×9.8 mm oblong punches. The compression procedure is same as Example 1.

The dissolution rate of the novel dosage form was determined (Table 3 and 4)

TABLE 3

Dissolution profile of tablet (A)

| Sodium valproate | | Lamotrigine | |
| --- | --- | --- | --- |
| Time (hour) | % Released | Time (min) | % Released |
| 1 | 23.3 | 15 | 83.5 |
| 2 | 36.3 | 30 | 88.6 |
| 4 | 55.1 | 45 | 91.6 |
| 6 | 67.5 | 60 | 92.8 |
| 8 | 77.0 | | |
| 10 | 83.8 | | |
| 12 | 88.9 | | |
| 14 | 92.5 | | |
| 24 | 104.6 | | |

TABLE 4

Dissolution profile of tablet (B)

| Sodium valproate | | Lamotrigine | |
| --- | --- | --- | --- |
| Time (hour) | % Released | Time (min) | % Released |
| 1 | 19.0 | 15 | 90.3 |
| 2 | 29.5 | 30 | 95.6 |

TABLE 4-continued

Dissolution profile of tablet (B)

| Sodium valproate | | Lamotrigine | |
|---|---|---|---|
| Time (hour) | % Released | Time (min) | % Released |
| 4 | 45.2 | 45 | 98.3 |
| 6 | 55.9 | | |
| 8 | 65.0 | | |
| 10 | 71.9 | | |
| 12 | 77.8 | | |
| 14 | 82.4 | | |
| 24 | 95.8 | | |

Dosage forms described in the examples 3 and 4 are prepared by not coating the micro matrix particles of the outer portion but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 3

1) Production of Inner Portion
    Same as for Example 1
2) Production of Outer Portion
    77.76% w/w of niacin is mixed with 7.78% w/w of Eudragit RSPO (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.
2) Compression of Tablets
Tablet (A)—Same as for Example 1
Tablet (B)—Same as for Example 1
    The dissolution rate of the novel dosage form was determined (Table 5 and 6)

TABLE 5

Dissolution profile of tablet (A)

| Niacin | | Pravastatin sodium | |
|---|---|---|---|
| Time (hour) | % Released | Time (min) | % Released |
| 1 | 30.1 | 45 | 75.9 |
| 2 | 43.6 | 60 | 80.9 |
| 4 | 61.6 | | |
| 6 | 74.1 | | |
| 8 | 83.9 | | |
| 10 | 92.1 | | |
| 12 | 99.4 | | |
| 24 | 102.6 | | |

TABLE 6

Dissolution profile of tablet (B)

| Niacin | | Pravastatin sodium | |
|---|---|---|---|
| Time (hour) | % Released | Time (min) | % Released |
| 1 | 29.9 | 45 | 89.6 |
| 2 | 36.3 | 60 | 90.0 |

TABLE 6-continued

Dissolution profile of tablet (B)

| Niacin | | Pravastatin sodium | |
|---|---|---|---|
| Time (hour) | % Released | Time (min) | % Released |
| 4 | 52.8 | | |
| 6 | 63.4 | | |
| 8 | 73.5 | | |
| 10 | 77.8 | | |
| 12 | 84.5 | | |
| 24 | 90.5 | | |

Example 4

1) Production of Inner Portion
    Same as for Example 2
2) Production of Outer Portion
    77.76% w/w of sodium valproate is mixed with 7.78% w/w of Eudragit RSPO (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.
3) Compression of Tablets
Tablet (A)—Same as for Example 2
Tablet (B)—Same as for Example 2
    The dissolution rate of the novel dosage form was determined (Table 7 and 8)

TABLE 7

Dissolution profile of tablet (A)

| Sodium valproate | | Lamotrigine | |
|---|---|---|---|
| Time (hour) | % Released | Time (min) | % Released |
| 1 | 58.3 | 15 | 81.8 |
| 2 | 79.9 | 30 | 89.8 |
| 4 | 98.5 | 45 | 91.7 |
| 6 | 101.6 | 60 | 97.4 |

TABLE 8

Dissolution profile of tablet (B)

| Sodium valproate | | Lamotrigine | |
|---|---|---|---|
| Time (hour) | % Released | Time (min) | % Released |
| 1 | 50.2 | 15 | 86.1 |
| 2 | 69.1 | 30 | 87.3 |
| 4 | 91.0 | 45 | 92.6 |
| 6 | 101.3 | 60 | 98.3 |

Example 5

1) Production of Inner Portion
    5.89% w/w of rosiglitazone maleate is mixed with 55.89% w/w of lactose monohydrate and 22.22% w/w starch and the mixture is granulated in a binder of 2.78% w/w povidone and 2.78% w/w starch in water and then dried. The granules are sieved and mixed with 0.28% w/w magnesium stearate, 10.00% w/w sodium starch glycolate, 0.17% w/w ferric oxide yellow. This mixture is compressed to 90 mg weight tablets having a diameter of 6.35 mm.

2) Production of Outer Portion

A) Micro matrix particles—90.91% w/w of metformin hydrochloride is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

3) Compression of Tablets

Tablet (A)—90 mg granules of inner portion are pressed to tablets(equal to 4 mg rosiglitazone) using 6.35 mm round punches and 643 mg granules of outer portion (equal to 500 mg metformin hydrochloride)are compressed using 14.95×8.35 mm oblong punches.

Tablet (B)—90 mg granules of inner portion are pressed to tablets(equal to 4 mg rosiglitazone) using 6.35 mm round punches and 1286 mg granules of outer portion (equal to 1000 mg metformin hydrochloride)are compressed using 20.3×9.8 mm oblong punches.

The compression is done on press coater machine in such a manner that the resultant tablet has inner portion covered by the outer portion from all the sides except top surface that remains uncovered and the level of the inner portion and the outer portion is on the same surface.

The dissolution rate of the novel dosage form was determined (Table 9 and 10)

TABLE 9

Dissolution profile of tablet (A)

| Metformin hydrochloride | | Rosiglitazone | |
|---|---|---|---|
| Time (hour) | % Released | Time (min) | % Released |
| 1 | 42.5 | 15 | 84.88 |
| 2 | 58.0 | 30 | 99.02 |
| 4 | 74.09 | 45 | 101.26 |
| 6 | 86.1 | 60 | 104.4 |
| 8 | 97.8 | | |
| 10 | 101.9 | | |
| 12 | 103.7 | | |

TABLE 10

Dissolution profile of tablet (B)

| Metformin hydrochloride | | Rosiglitazone | |
|---|---|---|---|
| Time (hour) | % Released | Time (min) | % Released |
| 1 | 38.2 | 45 | 96.79 |
| 2 | 53.4 | 60 | 99.32 |
| 4 | 69.5 | | |
| 6 | 78.1 | | |
| 8 | 86.8 | | |
| 10 | 93.6 | | |
| 12 | 97.65 | | |

Example 6

1) Production of Inner Portion

Same as for Example 5

2) Production of Outer Portion

A) Micro matrix particles—86.96% w/w of metformin hydrochloride is mixed with 13.07% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—86.40% w/w of micro matrix particles is charged in fluidized bed processor. 13.15% w/w of hydrogenated castor oil is dissolved in acetone and this coating solution is sprayed to coat the micro matrix particles. The coated micro matrix particles are sieved and mixed with 0.45% w/w magnesium stearate.

3) Compression of Tablets 90 mg granule of inner portion are pressed to tablets (equivalent to 4 mg rosiglitazone) using 6.35 mm round punches and 1331 mg granules of outer portion (equivalent to 1000 mg metformin hydrochloride) are compressed using 20.3×9.8 mm oval punches. The compression procedure is same as Example 5.

The dissolution rate of the novel dosage form was determined (Table 11)

TABLE 11

Dissolution profile

| Metformin Hydrochloride | | Rosiglitazone Maleate | |
|---|---|---|---|
| Time (hour) | % Released | Time (min) | % Released |
| 1 | 32.10 | 15 | 75.63 |
| 2 | 41.65 | 30 | 88.35 |
| 4 | 59.05 | 45 | 103.49 |
| 6 | 63.90 | 60 | 105.70 |
| 8 | 73.63 | | |
| 10 | 79.35 | | |
| 12 | 84.21 | | |
| 24 | 94.91 | | |

Example 7

1) Production of Inner Portion

Same as for Example 5

2) Production of Outer Portion

A) Micro matrix particles—

Same as for Example 5

B) Coating of Micro matrix particles—89.36% w/w of micro matrix particles is charged in fluidized bed processor. 10.15% w/w of glycerol distearate type 1 Ph. Eur. (Precirol ATO 5 R.T.M.) is dissolved in acetone and this coating solution is sprayed to coat the micro matrix particles. The coated micro matrix particles are sieved and mixed with 0.49% w/w magnesium stearate.

3) Compression of Tablets 90 mg granule of inner portion are pressed to tablets (equal to 4 mg rosiglitazone maleate) using 6.35 mm round punches and 1231 mg granules of outer portion (equal to 1000 mg metformin hydrochloride) are compressed using 20.3×9.8 mm oval punches. The compression procedure is same as Example 5.

The dissolution rate of the novel dosage form was determined (Table 12)

TABLE 12

| Dissolution profile | | | |
|---|---|---|---|
| Metformin Hydrochloride | | Rosiglitazone Maleate | |
| Time (hour) | % Released | Time (min) | % Released |
| 1 | 39.9 | 15 | 78.32 |
| 2 | 51.7 | 30 | 89.15 |
| 4 | 69.2 | 45 | 97.13 |
| 6 | 82.5 | 60 | 100.57 |
| 8 | 83.8 | | |
| 10 | 91.2 | | |
| 12 | 94.9 | | |
| 24 | 99.8 | | |

Example 8

1) Production of Inner Portion 2.94% w/w of rosiglitazone maleate is mixed with 87.80% w/w of Mannitol (Pearlitol SD 200 R.T.M.), 6.67% w/w of crosspovidone, 2.0% w/w of magnesium stearate, 0.56% w/w of colloidal silicon dioxide and 0.03% w/w ferric oxide red. This mixture is compressed to 90 mg weight tablets having a diameter of 6.35 mm.

2) Production of Outer Portion

Same as of Example 5.

3) Compression of Tablets 90 mg granule of inner portion are pressed to tablets (equal to 2 mg rosiglitazone maleate) using 6.35 mm round punches and 1281 mg granules of outer portion (equal to 1000 mg metformin hydrochloride) are compressed using 20.3×9.8 mm oval punches. The compression procedure is same as Example 5.

The dissolution rate of the novel dosage form was determined (Table 13)

TABLE 13

| Dissolution profile | | | |
|---|---|---|---|
| Metformin Hydrochloride | | Rosiglitazone Maleate | |
| Time (hour) | % Released | Time (min) | % Released |
| 1 | 38.29 | 15 | 80.2 |
| 2 | 53.40 | 30 | 96.1 |
| 4 | 69.51 | 45 | 103.4 |
| 6 | 78.11 | | |
| 8 | 86.86 | | |
| 10 | 93.60 | | |
| 12 | 97.65 | | |
| 24 | 100.17 | | |

Example 9

1) Production of Inner Portion 1.11% w/w of glimepiride is mixed with 63.28% w/w of lactose monohydrate and 22.22% w/w starch and the mixture is granulated in a binder of 2.22% w/w povidone in water and then dried. The granules are sieved and mixed with 1.11% w/w magnesium stearate, 10.0% w/w sodium starch glycolate, 0.06% w/w lake of brilliant blue. This mixture is compressed to 90 mg weight tablets having a diameter of 6.35 mm.

2) Production of Outer Portion

A) Micro matrix particles—83.33% w/w of metformin hydrochloride is mixed with 16.67% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—86.46% w/w of micro matrix particles is charged in fluidized bed processor. 12.61% w/w of hydrogenated castor oil is dissolved in acetone and this coating solution is sprayed to coat the micro matrix particles. The coated micro matrix particles are sieved and mixed with 0.91% w/w magnesium stearate.

3) Compression of Tablets 90 mg granule of inner portion are pressed to tablets(equal to 1 mg glimepiride) using 6.35 mm round punches and 694 mg granules of outer portion (equal to 500 mg metformin hydrochloride)are compressed using 14.95×8.35 mm oblong punches. The compression procedure is same as Example 5.

The dissolution rate of the novel dosage form was determined (Table 14)

TABLE 14

| Dissolution profile | | | |
|---|---|---|---|
| Metformin Hydrochloride | | Glimepiride | |
| Time (hour) | % Released | Time (min) | % Released |
| 1 | 28.0 | 15 | 69.4 |
| 2 | 40.5 | 30 | 91.87 |
| 4 | 57.8 | 45 | 99.64 |
| 6 | 65.8 | 60 | 103.87 |
| 8 | 73.2 | | |
| 10 | 80.3 | | |
| 12 | 85.0 | | |
| 24 | 101.8 | | |

Example 10

1) Production of Inner Portion

Same as for Example 5

2) Production of Outer Portion

C) Micro matrix particles—

Same as for Example 5

B) Coating of Micro matrix particles—91.21% w/w of micro matrix particles and 8.29% w/w of hydrogenated castor oil is mixed and charged in planetary mixer which is heated from outside to maintain the temperature approximately 80° C. with the help of a water bath. The above blend is mixed by running the planetary mixer for 1 hour to coat the micro matrix particles. The coated micro matrix particles are sieved and mixed with 0.50% w/w magnesium stearate.

3) Compression of Tablets 90 mg granule of inner portion are pressed to tablets (equal to 4 mg rosiglitazone maleate) using 6.35 mm round punches and 1206 mg granules of outer portion (equal to 1000 mg metformin hydrochloride) are compressed using 20.3×9.8 mm oval punches. The compression procedure is same as Example 5.

The dissolution rate of the novel dosage form was determined (Table 15)

TABLE 15

Dissolution profile

| Metformin Hydrochloride | | Rosiglitazone maleate | |
|---|---|---|---|
| Time (hour) | % Released | Time (min) | % Released |
| 1 | 25.7 | 30 | 85.9 |
| 2 | 36.6 | 45 | 100.3 |
| 4 | 49.1 | 60 | 104.9 |
| 6 | 57.5 | | |
| 8 | 66.5 | | |
| 10 | 71.3 | | |
| 12 | 76.0 | | |
| 14 | 90.7 | | |

Dosage forms described in the example 11 are prepared by not coating the micro matrix particles of the outer portion but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 11

1) Production of Inner Portion
   Same as for Example 5
2) Production of Outer Portion 77.76% w/w of metformin hydrochloride is mixed with 7.780 % w/w of Eudragit RS (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.

3) Compression of Tablets
Tablet (A)—Same as for Example 5
Tablet (B)—Same as for Example 5

The dissolution rate of the novel dosage form was determined (Table 16 and 17)

TABLE 16

Dissolution profile of tablet (A)

| Metformin hydrochloride | | Rosiglitazone | |
|---|---|---|---|
| Time (hour) | % Released | Time (min) | % Released |
| 1 | 63.9 | 15 | 100.08 |
| 2 | 85.5 | 30 | 106.41 |
| 4 | 102.1 | 45 | 109.77 |

TABLE 17

Dissolution profile of tablet (B)

| Metformin hydrochloride | | Rosiglitazone | |
|---|---|---|---|
| Time (hour) | % Released | Time (min) | % Released |
| 1 | 50.3 | 15 | 99.22 |
| 2 | 70.5 | 30 | 105.26 |
| 4 | 88.0 | 45 | 107.53 |
| 6 | 100.9 | 60 | 107.53 |

Example 12

1) Production of Inner Portion
   Same as for Example 7.
2) Production of Outer Portion
A) Micro matrix particles—93.02% w/w of metformin hydrochloride is mixed with 6.98% w/w of Eudragit RS (Ammonio Methacrylate Copolymer type B USP) and the mixture is granulated with a solvent mixture of acetone and methylene chloride and then dried. The granules are sized.
B) Coating of Micro matrix particles—85.18% w/w of micro matrix particles is charged in fluidized bed processor. 13.87% w/w of hydrogenated castor oil is dissolved in acetone and this coating solution is sprayed to coat the micro matrix particles. The coated micro matrix particles are sieved and mixed with 0.95% w/w magnesium stearate.
3) Compression of Tablets 90 mg granule of inner portion are pressed to tablets (equal to 4 mg rosiglitazone) using 6.35 mm round punches and 1262 mg granules of outer portion (equal to 1000 mg metformin hydrochloride) are compressed using 20.3×9.8 mm oblong punches. The compression procedure is same as Example 5.

The dissolution rate of the novel dosage form was determined (Table 18)

TABLE 18

Dissolution profile

| Metformin Hydrochloride | | Rosiglitazone | |
|---|---|---|---|
| Time (hour) | % Released | Time (min) | % Released |
| 1 | 40.9 | 45 | 89.68 |
| 2 | 52.2 | 60 | 91.42 |
| 4 | 68.4 | | |
| 6 | 79.2 | | |
| 8 | 88.6 | | |
| 10 | 99.9 | | |
| 12 | 101.5 | | |

Example 13

1) Production of Inner Portion
   Same as for Example 7.
2) Production of Outer Portion
A) Micro matrix particles—Same as for Example 12.
B) Coating of Micro matrix particles—88.70% w/w of micro matrix particles is charged in fluidized bed processor. 10.31% w/w of hydrogenated castor oil is dissolved in acetone and this coating solution is sprayed to coat the micro matrix particles. The coated micro matrix particles are sieved and mixed with 0.99% w/w magnesium stearate.

3) Compression of Tablets 90 mg granule of inner portion are pressed to tablets(equal to 4 mg rosiglitazone) using 6.35 mm round punches and 1212 mg granules of outer portion (equal to 1000 mg metformin hydrochloride)are compressed using 20.3×9.8 mm oblong punches. The compression procedure is same as Example 5.

The dissolution rate of the novel dosage form was determined (Table 19)

TABLE 19

| Dissolution profile | | | |
|---|---|---|---|
| Metformin Hydrochloride | | Rosiglitazone | |
| Time (hour) | % Released | Time (min) | % Released |
| 1 | 44.50 | 15 | 79.9 |
| 2 | 58.90 | 30 | 89.9 |
| 4 | 76.90 | 45 | 95.8 |
| 6 | 91.40 | 60 | 100.6 |
| 8 | 102.40 | | |

Example 14

1) Production of Inner Portion

Same as for Example 11.

2) Production of Outer Portion

A) Micro matrix particles—Same as for Example 12.

B) Coating of Micro matrix particles—90.56% w/w of micro matrix particles is charged in fluidized bed processor. 8.42% w/w of hydrogenated castor oil is dissolved in acetone and this coating solution is sprayed to coat the micro matrix particles. The coated micro matrix particles are sieved and mixed with 1.01% w/w magnesium stearate.

3) Compression of Tablets 90 mg granule of inner portion are pressed to tablets(equal to 4 mg rosiglitazone) using 6.35 mm round punches and 1187 mg granules of outer portion (equal to 1000 mg metformin hydrochloride)are compressed using 20.3×9.8 mm oblong punches. The compression procedure is same as Example 5.

The dissolution rate of the novel dosage form was determined (Table 20)

TABLE 20

| Dissolution profile | | | |
|---|---|---|---|
| Metformin Hydrochloride | | Rosiglitazone | |
| Time (hour) | % Released | Time (min) | % Released |
| 1 | 42.40 | 45 | 86.05 |
| 2 | 58.1 | 60 | 90.73 |
| 4 | 75.9 | | |
| 6 | 86.5 | | |
| 8 | 94.5 | | |
| 10 | 99.0 | | |

Example 15

1) Production of Inner Portion

Same as for Example 7.

2) Production of Outer Portion

A) Micro matrix particles—90.91% w/w of metformin hydrochloride is mixed with 4.55% w/w of Eudragit RS (Ammonio Methacrylate Copolymer type B USP) and 4.55% w/w of Eudragit RL (Ammonio Methacrylate Copolymer type A USP) and the mixture is granulated with a solvent mixture of acetone and methylene chloride and then dried. The granules are sized.

B) Coating of Micro matrix particles—85.47% w/w of micro matrix particles is charged in fluidized bed processor. 13.60% w/w of hydrogenated castor oil is dissolved in acetone and this coating solution is sprayed to coat the micro matrix particles. The coated micro matrix particles are sieved and mixed with 0.93% w/w magnesium stearate.

3) Compression of Tablets 90 mg granule of inner portion are pressed to tablets(equal to 4 mg rosiglitazone) using 6.35 mm round punches and 1287 mg granules of outer portion (equal to 1000 mg metformin hydrochloride)are compressed using 20.3×9.8 mm oblong punches. The compression procedure is same as Example 5.

The dissolution rate of the novel dosage form was determined (Table 21)

TABLE 21

| Dissolution profile | | | |
|---|---|---|---|
| Metformin Hydrochloride | | Rosiglitazone | |
| Time (hour) | % Released | Time (min) | % Released |
| 1 | 34.8 | 45 | 92.65 |
| 2 | 48.3 | 60 | 97.02 |
| 4 | 66.2 | | |
| 6 | 79.3 | | |
| 8 | 85.9 | | |
| 10 | 92.6 | | |
| 12 | 97.6 | | |

Example 16

1) Production of Inner Portion

Same as for Example 7.

2) Production of Outer Portion

A) Micro matrix particles—Same as for Example 15.

B) Coating of Micro matrix particles—94.66% w/w of micro matrix particles is charged in fluidized bed processor. 4.30% w/w of hydrogenated castor oil is dissolved in acetone and this coating solution is sprayed to coat the micro matrix particles. The coated micro matrix particles are sieved and mixed with 1.03% w/w magnesium stearate.

3) Compression of Tablets 90 mg granule of inner portion are pressed to tablets(equal to 4 mg rosiglitazone) using 6.35 mm round punches and 1162 mg granules of outer portion (equal to 1000 mg metformin hydrochloride)are compressed using 20.3×9.8 mm oblong punches. The compression procedure is same as Example 5.

The dissolution rate of the novel dosage form was determined (Table 22)

TABLE 22

Dissolution Profile

| Metformin Hydrochloride | | Rosiglitazone | |
|---|---|---|---|
| Time (hour) | % Released | Time (min) | % Released |
| 1 | 47.56 | 45 | 92.94 |
| 2 | 61.93 | 60 | 96.70 |
| 4 | 82.42 | | |
| 6 | 96.0 | | |
| 8 | 100.0 | | |

Example 17

1) Production of Inner Portion
   Same as for Example 7.
2) Production of Outer Portion
A) Micro matrix particles—Same as for Example 5.
B) Coating of Micro matrix particles—88.92% w/w of micro matrix particles is charged in fluidized bed processor. 10.11% w/w of hydrogenated castor oil is dissolved in acetone and this coating solution is sprayed to coat the micro matrix particles. The coated micro matrix particles are sieved and mixed with 0.97% w/w magnesium stearate.
3) Compression of Tablets
   90 mg granule of inner portion are pressed to tablets(equal to 4 mg rosiglitazone) using 6.35 mm round punches and 1237 mg granules of outer portion (equal to 1000 mg metformin hydrochloride)are compressed using 20.3×9.8 mm oblong punches. The compression procedure is same as Example 5.

The dissolution rate of the novel dosage form was determined (Table 23)

TABLE 23

Dissolution profile

| Metformin Hydrochloride | | Rosiglitazone | |
|---|---|---|---|
| Time (hour) | % Released | Time (min) | % Released |
| 1 | 35.0 | 15 | 69.2 |
| 2 | 47.3 | 30 | 79.5 |
| 4 | 60.8 | 45 | 85.7 |
| 6 | 72.5 | 60 | 90.4 |
| 8 | 81.8 | | |
| 10 | 89.2 | | |
| 12 | 94.1 | | |
| 24 | 98.2 | | |

Example 18

1) Production of Inner Portion
   Same as for Example 7.
2) Production of Outer Portion
A) Micro matrix particles—Same as for Example 5.
B) Coating of Micro matrix particles—87.09% w/w of micro matrix particles is charged in fluidized bed processor. 11.88% w/w of hydrogenated castor oil is dissolved in acetone and this coating solution is sprayed to coat the micro matrix particles. The coated micro matrix particles are sieved and mixed with 1.03% w/w magnesium stearate.
3) Compression of Tablets
   90 mg granule of inner portion are pressed to tablets(equal to 4 mg rosiglitazone) using 6.35 mm round punches and 1263 mg granules of outer portion (equal to 1000 mg metformin hydrochloride)are compressed using 20.3×9.8 mm oblong punches. The compression procedure is same as Example 5.

The dissolution rate of the novel dosage form was determined (Table 24)

TABLE 24

Dissolution profile

| Metformin Hydrochloride | | Rosiglitazone | |
|---|---|---|---|
| Time (hour) | % Released | Time (min) | % Released |
| 1 | 38.7 | 30 | 78.66 |
| 2 | 52.9 | 45 | 83.47 |
| 4 | 71.6 | 60 | 88.06 |
| 6 | 82.3 | | |
| 8 | 91.3 | | |
| 10 | 97.3 | | |
| 12 | 101.1 | | |

Example 19

1) Production of Inner Portion
   2.22% w/w of glimepiride is mixed with 62.17% w/w of lactose monohydrate and 22.22% w/w starch and the mixture is granulated in a binder of 2.22% w/w povidone in water and then dried. The granules are sieved and mixed with 0.56% w/w magnesium stearate, 10.0% w/w sodium starch glycolate, 0.06% w/w lake of erythrocine and 0.56% w/w colloidal silicon dioxide. This mixture is compressed to 90 mg weight tablets having a diameter of 6.35 mm.
2) Production of Outer Portion—Same as for Example 18
3) Compression of Tablets
   90 mg granule of inner portion are pressed to tablets(equal to 2 mg glimepiride) using 6.35 mm round punches and 1263 mg granules of outer portion (equal to 1000 mg metformin hydrochloride) are compressed using 20.3×9.8 mm oblong punches. The compression procedure is same as Example 5.

The dissolution rate of the novel dosage form was determined (Table 25)

TABLE 25

Dissolution profile

| Metformin Hydrochloride | | Glimepiride | |
|---|---|---|---|
| Time (hour) | % Released | Time (min) | % Released |
| 1 | 38.79 | 45 | 100.7 |
| 2 | 54.12 | 60 | 102.2 |
| 4 | 69.54 | | |
| 6 | 82.04 | | |
| 8 | 89.78 | | |
| 10 | 95.06 | | |
| 12 | 100.48 | | |

Example 20

Determination of Relative Bioavailability of Metformin Sustained Release Formulation With Respect to Metformin Immediate Release Tablet The study was carried out to demonstrate the sustained release characteristic of metformin in the combination formulation and to evaluate the relative bioavailability of combination formulation of sustained release Metformin hydrochloride and Rosiglitazone maleate versus metformin immediate release tablet 2×500 mg (marketed as Glycomet® by USV Ltd.; India.) and rosiglitazone immediate release tablets 4 mg (marketed as Enselin® by Torrent pharma Ltd.; India.).

Methodology

The biostudy had an open label, randomized two period, two treatment, two way single dose crossover study with 7 days washout period between treatment days.

Non-compartmental Pharmacokinetic assessment was based on the plasma levels of Metformin and Rosiglitazone measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Number of Subjects and Study Population:

Twelve (12) volunteers were enrolled and all of them completed the study. All 12 volunteers were included in the Pharmacokinetic and safety analyses.

Criteria for Inclusion:

Healthy male volunteers aged between 18 to 45 years.

Test Formulation, Dose and Mode of Administration:

Test Formulation: 4 mg/1000 mg Rosiglitazone/Metformin SR prepared as per the invention disclosed in the examples. Volunteers received a single oral dose of above products with 200 ml of water following high calorie diet (~800 Kcal).

Reference Product, Dose and Mode of Administration:

Reference: Immediate release 4 mg Enselin® plus Glycomate® (2×500 mg)

Volunteers received a single oral dose of above products with 200 ml of water following high calorie diet (~800 Kcal).

Pharmacokinetics:

The following Pharmacokinetic parameters were calculated using non compartments methods: the area under the drug plasma concentration curve from time of dosing to the time of last sampling point ($AUC_{(0-t)}$); the area under the drug plasma concentration versus time curve extrapolated to infinity ($AUC_{(0-Inf...)}$); the maximum measured concentration of the drug in the plasma ($C_{max}$) and the time at which this concentration was measured ($t_{max}$); the concentration at 24 hours ($C_{24h}$); the time taken for drug plasma concentration to decrease by 50% ($t_{1/2}$); and the terminal first-order elimination rate constant ($K_{el}$).

Area Under the curve (AUC) is the integral part of drug blood level over time from zero to infinity and is a measure of quantity of drug absorbed and in the body.

AUC(0-t) represents area under the curve from zero to time t, where t represents the time at which last blood sample was taken.

$AUC_{(0-Inf)}$ represents area under the curve from zero to infinity.

Elimination half life of a drug is the time in hours necessary to reduce the drug concentration in the blood, plasma or serum to ½ after equilibrium is reached.

$C_{max}$ is the peak plasma concentration achieved after the administration of the drug.

$T_{max}$ is the time to reach peak plasma concentration.

Statistical Methods:

Descriptive statistics of relevant Pharmacokinetic parameters were performed. An analysis of variance (ANOVA) was used to assess treatment differences.

Methods Used for Analysis of Metformin and Rosiglitazone in Plasma Samples:

Analysis of Metformin:

Estimation of Metformin in plasma samples was carried out by High Performance Liquid Chromatography and UV detection at 234 nm. Briefly 0.5 ml of plasma sample was precipitated with 2.0 ml acetonitrile. Samples were centrifuged and supernatant aliquot was washed with dichloromethane. After centrifugation, aqueous layer was injected on HPLC.

Analysis of Rosiglitazone:

Estimation of Rosiglitazone in plasma samples was carried out by LC-MS/MS. Briefly 0.1 ml of plasma sample was precipitated with 0.25 ml acetonitrile. Samples were centrifuged and supernatant aliquot was analyzed by LC-MS/MS.

Figure 8:
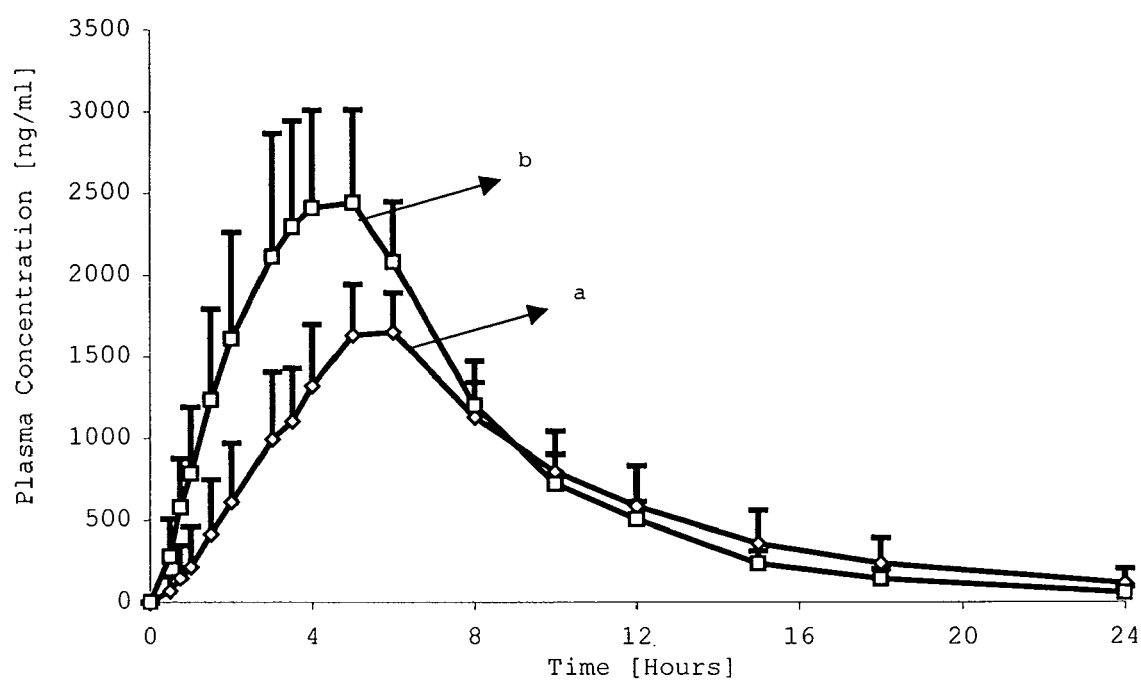
FIG. 8 is a plot of metformin plasma concentration versus time for test (a) and reference (b) formulation.
Figure 9:
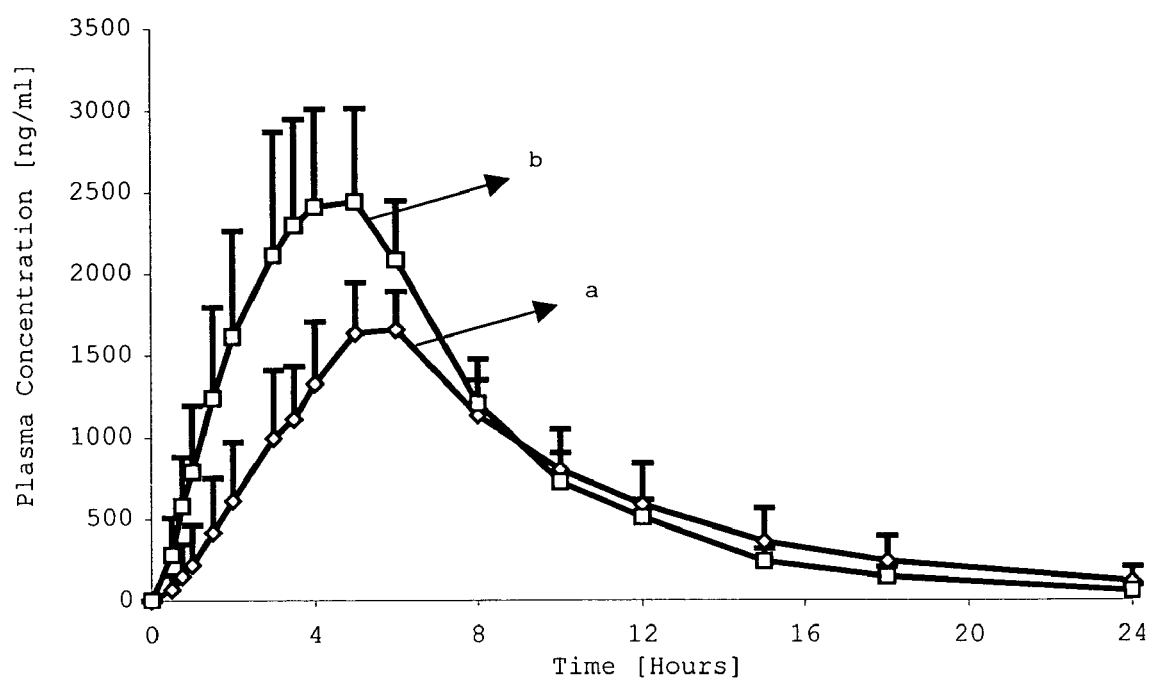
FIG. 9 is a plot of rosiglitazone plasma concentration versus time for test (a) and reference (b) formulation.

Pharmacokinetic Results:

The summary of the statistical analysis and confidence intervals of the Pharmacokinetic parameters is contained in Tables 26 & 27. The mean plasma concentration versus time curve is depicted in FIG. 8 (metformin) & FIG. 9 rosiglitazone) wherein curve a represents Test Formulation and curve b represents Reference Formulation.

TABLE 26

Bioavailability Summary and Analysis - Metformin SR (1000 mg)

| Parameters | Unit | Test | Reference |
|---|---|---|---|
| $AUC_{0-inf}$ | ng * hr/ml | 15980 ± 3456 | 19551 ± 4265 |
| $AUC_{0-t}$ | ng * hr/ml | 14983 ± 2930 | 19091 ± 4200 |
| $C_{max}$ | ng/ml | 1737.61 ± 249.09 | 2558.37 ± 623.05 |
| $C_{24h}$ | ng/ml | 113.87 ± 91.05 | 56.44 ± 37.94 |
| $T_{max}$ | hr | 5.42 ± 0.68 | 4.42 ± 0.88 |
| $T_{1/2}$ | hr | 4.71 ± 1.36 | 4.26 ± 1.14 |

TABLE 27

Bioavailability Summary and Analysis - Rosiglitazone (4 mg)

| Parameters | Unit | Test | Reference |
|---|---|---|---|
| $AUC_{0-inf}$ | ng * hr/ml | 1851 ± 414 | 1730 ± 465 |
| $AUC_{0-t}$ | ng * hr/ml | 1795 ± 401 | 1676 ± 438 |
| $C_{max}$ | ng/ml | 243.48 ± 40.78 | 247.48 ± 45.38 |
| $C_{24h}$ | ng/ml | 6.36 ± 5.19 | 3.37 ± 4.36 |
| $T_{max}$ | hr | 3.75 ± 1.03 | 3.25 ± 1.66 |
| $t_{1/2}$ | hr | 3.73 ± 0.60 | 3.63 ± 0.79 |

Conclusion:

Metformin in test formulation has shown sustained release characteristics with lower $C_{max}$ and prolonged $t_{max}$ (FIG. 8). The relative bioavailability of both the components was studied.

Example 21

Determination of Relative Bioavailability of Two Formulations With Different Release Profiles:

A biostudy was carried out with the preliminary objective of comparing the relative bioavailability of the 1000 mg metformin sustained release formulations (A & B) relative to immediate release metformin tablets 2×500 mg (marketed as Glycomet® by USV Ltd.; India.). A secondary objective was to characterize the plasma concentration profile of metformin in the sustained release formulation relative to immediate release formulation i.e. Glycomet® 2×500 mg tablets.

Methodology:

The biostudy had an open label, randomized, three periods, three treatment, three way, single dose crossover design with 7 days washout period between treatment days.

Non-compartmental Pharmacokinetic assessment was based on the plasma levels of metformin measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Number of Subjects and Study Population:

Twelve (12) volunteers were enrolled and 11 of them completed the study. All 12 volunteers were included in the Pharmacokinetic and safety analyses.

Criteria for Inclusion:

Healthy male volunteers aged between 18 to 45 years.

Test Product, Dose and Mode of Administration:

Formulation A: 4 mg/1000 mg Rosiglitazone/Metformin dosage form prepared as per the invention disclosed in the examples.

Formulation B: 4 mg/1000 mg Rosiglitazone/Metformin SR dosage form prepared as per the invention disclosed in the examples.

In the morning, volunteers received a single oral dose of above products with 200 ml of water following high calorie diet (~800 Kcal).

Reference Product, Dose and Mode of Administration:

Formulation C: Immediate release 4 mg Enselin® plus Glycomate® (2×500 mg)

In the morning, volunteers received a single oral dose of above products with 200 ml of water following high calorie diet (~800 Kcal).

Pharmacokinetics:

Same as for example 20.

Statistical Methods:

Same as for example 20.

Methods Used for Analysis of Metformin and Rosiglitazone in Plasma Samples:

Same as for example 20.

Figure 10:
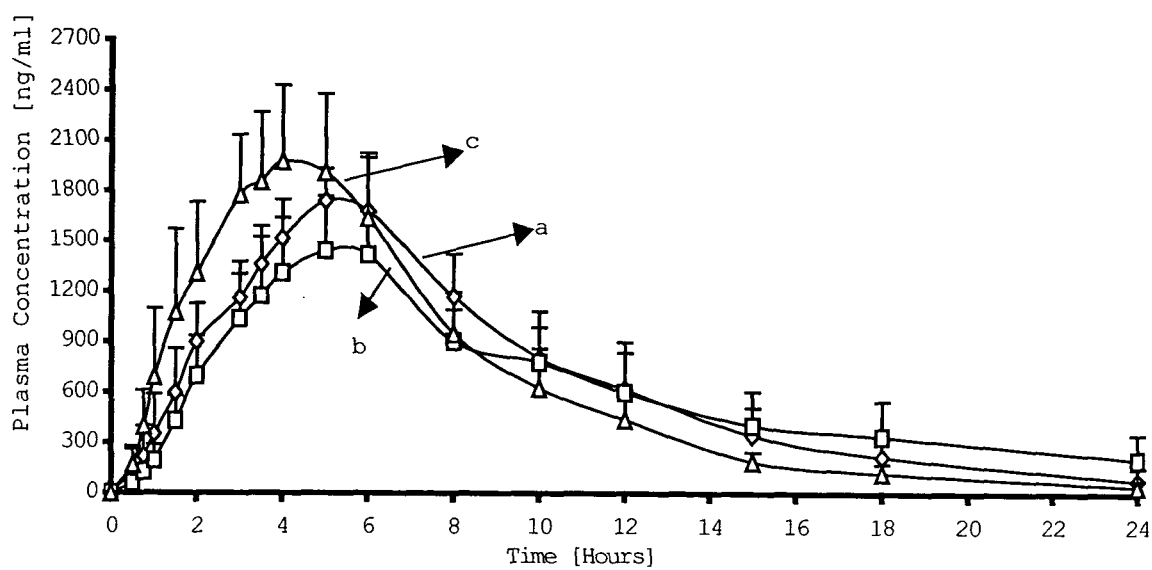
FIG. 10 is a plot of metformin plasma concentration versus time for test (a and b) and reference (c) formulation.

Pharmacokinetic Results:

The summary of the statistical analysis and confidence intervals of the Pharmacokinetic parameters is contained in Table 28. The mean plasma concentration versus time curve is depicted in FIG. 10. wherein curve a represents Formulation A, curve b represents Formulation B and curve c represents the Formulation C.

TABLE 28

Bioavailability Summary and Analysis - Metformin SR (1000 mg)

| Parameters | Unit | Formulation A | Formulation B | Formulation C |
|---|---|---|---|---|
| $AUC_{0-inf}$ | ng * hr/ml | 16508 ± 3655 | 17762 ± 5113 | 15985 ± 2886 |
| $AUC_{0-t}$ | ng * hr/ml | 15899 ± 3270 | 14989 ± 3196 | 15558 ± 2930 |
| $C_{max}$ | ng/ml | 1801.72 ± 264.82 | 1551.01 ± 337.49 | 2121.96 ± 405.95 |
| $C_{24h}$ | ng/ml | 79.58 ± 75.10 | 204.96 ± 151.02 | 45.48 ± 37.99 |
| $T_{max}$ | Hr | 5.36 ± 0.51 | 5.46 ± 0.78 | 4.00 ± 0.74 |
| $T_{1/2}$ | Hr | 4.08 ± 1.32 | 7.23 ± 3.45 | 4.61 ± 1.54 |

Conclusion:

Both the formulations according to the invention tested had reduced $C_{max}$ compared to that of the reference product (Glycomet® tablets), with Formulation B being significantly reduced. The $t_{max}$ of both the formulations according to invention were prolonged relative to that of Glycomet® tablets. The concentration at 24 hours ($C_{24h}$) of Formulation B was almost 4.5 times higher than Glycomet® tablets and almost 2.6 times higher than Formulation A.

Example 22

Determination of Relative Bioavailability of Metformin Sustained Release Formulations The study was carried out to assess the effect of night time administration and to evaluate the relative bioavailability of combination formulation of sustained release Metformin and Rosiglitazone (prepared as per the invention disclosed in the examples) versus metformin sustained release tablet (marketed as Glucophage XR® by Bristol Myers Squibb; USA.) and rosiglitazone immediate release tablet (marketed as Avandia® by Glaxo Smithkline; United Kingdom.).

Methodology:

The biostudy had an open label, randomized two period, two treatment, two way single dose crossover study with 7 days washout period between treatment days.

Non-compartmental Pharmacokinetic assessment was based on the plasma levels of Metformin and Rosiglitazone measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Number of Subjects and Study Population:

Sixteen (16) volunteers were enrolled and 15 of them completed the study. All 15 volunteers were included in the Pharmacokinetic and safety analyses.

Criteria for Inclusion:

Healthy male volunteers aged between 18 to 45 years.

Test Product, Dose and Mode of Administration:

Test Formulation: 4 mg/1000 mg Rosiglitazone/Metformin sustained release dosage form prepared as per the invention disclosed in the examples. Volunteers received a single oral dose of above products with 200 ml of water following high calorie dinner (~1400 KCal).

Figure 11:
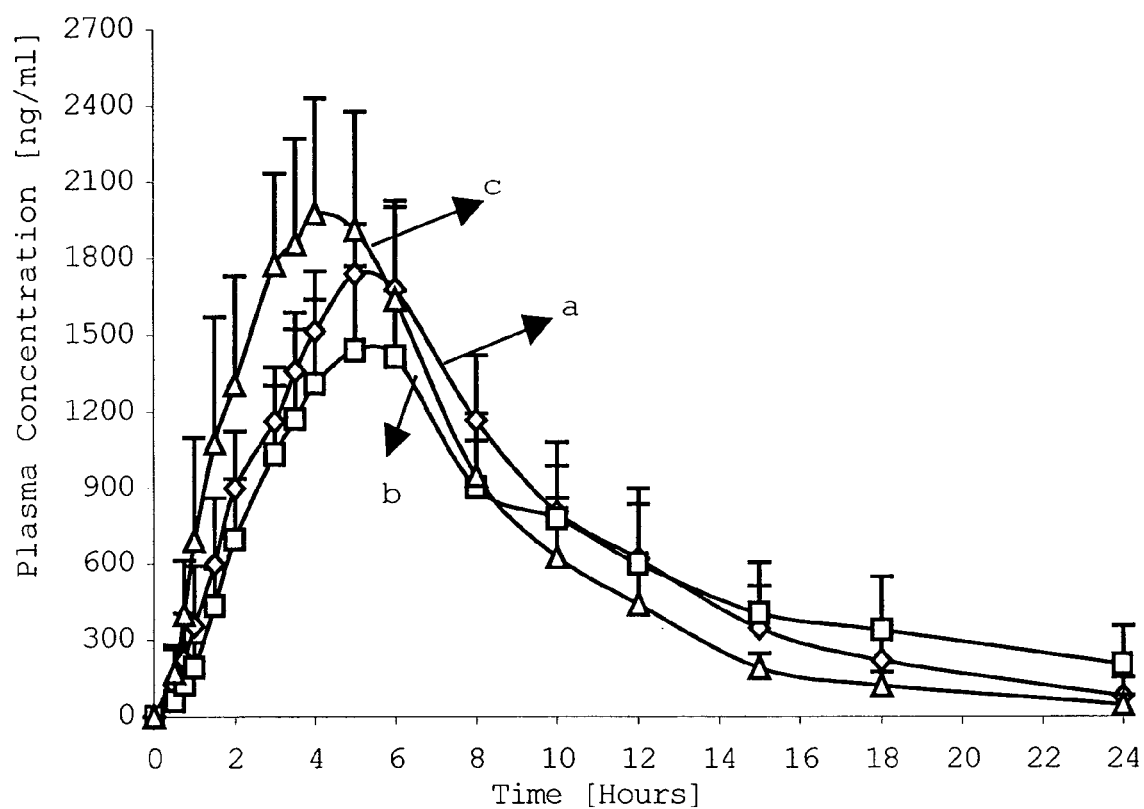
FIG. 11 is a plot of metformin plasma concentration versus time for test (a) and reference (b) formulation.

Reference Product, Dose and Mode of Administration:
Reference: 4 mg Avandia® plus Glucophage XR® (2×500 mg) Volunteers received a single oral dose of above products with 200 ml of water following calorie dinner (~1400 Kcal).
Pharmacokinetics:
Same as for example 20.
Statistical Methods:
Descriptive statistics of relevant Pharmacokinetic parameters were performed. An analysis of variance (ANOVA) was used to assess treatment differences.
Westlake's 90% confidence interval for the ratio of two formulations for log transformed data were calculated, and to test that the difference between two formulations are within the (80 to 125%) limits.
Methods Used for Analysis of Metformin and Rosiglitazone in Plasma Samples:
Same as for example 20.
Pharmacokinetic Results:
The summary of the statistical analysis and confidence intervals of the Pharmacokinetic parameters is contained in Table 29 & 30. The mean plasma concentration versus time curve is depicted in FIGS. 11 (Metformin) & 12 (Rosiglitazone) wherein curve a represents Test Formulation and curve b represents Reference Formulation.

TABLE 29

Bioavailability Summary and Analysis - Metformin SR (1000 mg)

| Parameters | Unit | Test | Reference | 90% Westlake Interval | |
| --- | --- | --- | --- | --- | --- |
| | | | | Upper | Lower |
| $AUC_{0-inf}$ | ng*hr/ml | 16939 ± 2323 | 16396 ± 3791 | 83.84 | 116.16 |
| $AUC_{0-t}$ | ng*hr/ml | 16107 ± 2114 | 15951 ± 3543 | 87.33 | 112.67 |
| $C_{max}$ | ng/ml | 1515.29 ± 225.97 | 1558.78 ± 364.23 | 90.89 | 109.11 |
| $C_{24h}$ | ng/ml | 120.10 ± 74.01 | 79.63 ± 60.22 | — | — |
| $T_{max}$ | hr | 7.64 ± 1.65 | 8.86 ± 1.03 | — | — |
| $T_{1/2}$ | hr | 4.12 ± 1.34 | 3.36 ± 0.70 | — | — |

TABLE 30

Bioavailability Summary and Analysis - Rosiglitazone (4 mg)

| Parameters | Unit | Test | Reference | 90% Westlake Interval | |
| --- | --- | --- | --- | --- | --- |
| | | | | Upper | Lower |
| $AUC_{0-inf}$ | ng*hr/ml | 1308 ± 432 | 1258 ± 331 | 85.73 | 114.27 |
| $AUC_{0-t}$ | ng*hr/ml | 1266 ± 400 | 1234 ± 324 | 86.61 | 113.39 |
| $C_{max}$ | ng/ml | 145.70 ± 48.90 | 161.83 ± 55.43 | 80.88 | 119.12 |
| $C_{24h}$ | ng/ml | 6.07 ± 7.46 | 1.80 ± 3.11 | — | — |
| $T_{max}$ | hr | 5.07 ± 2.63 | 4.13 ± 1.91 | — | — |
| $T_{1/2}$ | hr | 3.59 ± 0.71 | 3.32 ± 0.59 | — | — |

Figure 12:
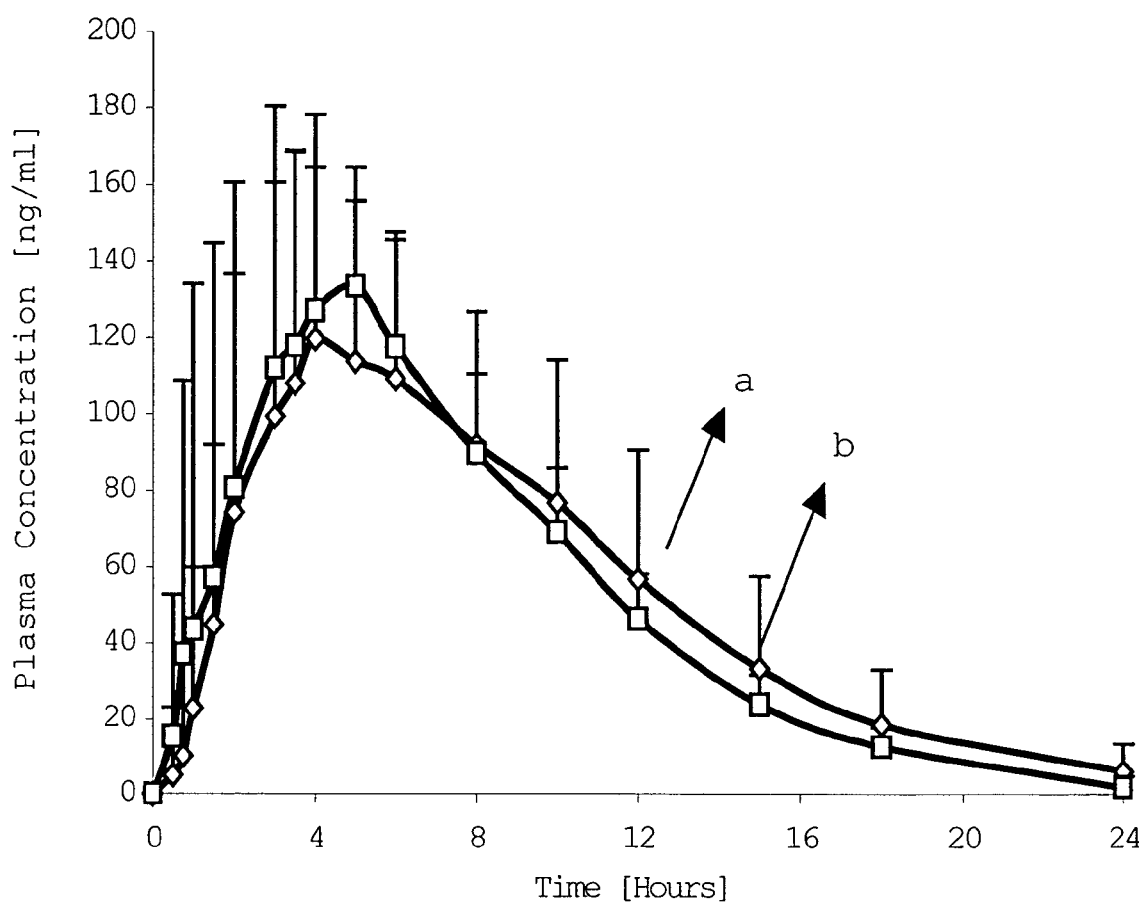
FIG. 12 is a plot of rosiglitazone plasma concentration versus time for test (a) and reference (b) formulation.

Conclusion:
The relative bioavailability study shown that bioequivalance was achieved between the 4 mg/1000 mg combination formulation and the respective components, for both AUC and $C_{max}$ parameters (Table 29 & 30). Moreover, in the test formulation, the concentration of Metformin at 24 hrs was almost 1.5 times more than Glucophage XR® (FIG. 11) wherein curve a represents Test formulation and b represents Reference formulation (Table 29). Similarly Rosiglitazone component of the test formulation also shown higher concentration at 24 hrs as that of Avandia® (FIG. 12; wherein curve a represents Test Formulation and curve b represents Reference Formulation and Table 30).

What is claimed is:

1. A pharmaceutical dosage form of a combination of a high dose high solubility active ingredient, in the form of a modified release formulation and a low dose active ingredient selected from the group consisting of glibenclamide (glyburide), glipizide, gliclazide, glimepiride, tolazamide, tolbutamide, clorpropamide, gliquidone, nateglinide, mitiglinide, glyburide, glisoxepid, glibornuride, phenbutamide, tolcyclamide, repaglinide, troglitazone, ciglitazone, rosiglitazone, pioglitazone, englitazone, acarbose, voglibose, emiglitate, miglitol, farglitazar, (S)-2-ethoxy-3-[4-(2-{4-methanesulfonyloxyphenyl} ethoxy) phenyl] propanoic acid, 3-{4-[2-4-tert-butoxycarbonyl aminophenyl)ethoxy]phenyl}-(S)-2-ethoxy propanoic acid and pharmaceutically acceptable salts thereof as an immediate release formulation suitable for swallowing; said dosage formulation comprising an inner portion having the low dose active ingredient as an immediate release formulation and an outer portion having the high dose, high solubility active ingredient as modified release, wherein said inner portion is covered by the outer portion from all the sides except a top surface that remains uncovered; wherein said outer portion is prepared by using dual retard technique to control the release of the high dose high solubility activity active ingredient, wherein the said dual retard technique is a combination of a matrix formulation and a reservoir formulation and comprises
    a) micro matrix particles consisting of a high dose, high solubility active ingredient and one or more hydrophobic release controlling agents wherein the weight ratio of high dose, high solubility active ingredient and hydrophobic release controlling agent is in the range of 100:2.5 to 100:30 and said high dose, high solubility active ingredient is selected from the group consisting of metformin hydrochloride, phenformin and buformin and,
    b) a coating of one or more hydrophobic release controlling agents on said micro matrix particles, wherein the weight ratio of micromatrix particles and hydrophobic release controlling agent is in the range of 100:2.5 to 100:30.

2. A dosage form according to claim 1, wherein the hydrophobic release controlling agents are selected from the group consisting of poly(ethyl acrylate, methyl methacrylate, trimethylammonioethyl methacrylate chloride) 1:2:0.1; poly (ethyl acrylate, methyl methacrylate, trimethylammonioethyl methacrylate chloride) 1:2:0.2 and poly(ethylacrylate, methyl methacrylate) 2:1 polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl actylate), poly (octadecyl acrylate), waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate, glycerol distearate, glycerol monooleate, acetylated monoglycerides, tristearin, tripalmitin, cetyl esters wax, glyceryl palmitostearate, glyceryl behenate and hydrogenated castor oil.

3. A dosage form according to claim 2, wherein the hydrophobic release controlling agent(e) is selected from the group consisting of ammonio methacrylate co-polymers.

4. A dosage form according to claim 3, wherein the ammonio methacrylate co-polymers are selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate 2:1.

5. A dosage form according to claim 1, wherein in micro matrix particles, the active ingredient and one or more hydrophobic release controlling agents are present in a weight ratio of from 100:2.5 to 100:30.

6. A dosage form according to claim 1, wherein said coating on said micro matrix particles consists of one or more hydrophobic release controlling agents.

7. A dosage form according to claim 1, wherein the hydrophobic release controlling agent(s) is selected from fatty acid esters.

8. A dosage form according to claim 7, wherein the hydrophobic release controlling agents is selected from the group consisting of hydrogenated castor oil and glycerol distearate.

9. A dosage form according to claim 1, wherein in outer portion, micro matrix particles and coating of one or more hydrophobic release controlling agents are present in a weight ratio of from 100:2.5 to 100:30.

10. A dosage form according to claim 1, wherein the weight ratio of immediate release active ingredient and modified release active ingredient is from 1:10 to 1:15000.

11. A dosage form according to claim 1, wherein the low dose active ingredient consist of dose less than or equal to 50 mg.

12. A dosage form according to claim 1, wherein the high dose, high solubility active ingredient consists of a dose from 500 mg to 1500 mg.

13. A dosage form according to claim 1, wherein the low dose antidiabetic active ingredient consist of a dose less than or equal to 50 mg.

14. dosage form according to claim 1, wherein the high dose high solubility antidiabetic active ingredient consists of a dose from 500 mg to 1500 mg.

15. A dosage form according to claim 1, which is a once a day oral formulation.

16. A dosage form according to claim 1, wherein the high dose high solubility antidiabetic active ingredient is metformin hydrochloride.

17. A dosage form according to claim 16, wherein the composition of outer portion is as follows—
Micro matrix particles—
Metformin hydrochloride 75% w/w to 99% w/w
poly(ethylacrylate, methyl
methacrylate, trimethylammonioethyl methacrylate
chloride 1:2:0.1 1% w/w to 25% w/w
Coated micro matrix particles
Micro matrix particles 70% w/w to 99% w/w
Hydrogenated castor oil 1% w/w to 30% w/w
Magnesium stearate 0% w/w to 2% w/w 18. A dosage form according to claim 1, wherein the low dose antidiabetic active ingredient is rosiglitazone maleate.

19. A dosage form according to claim 1, wherein the low dose antidiabetic active ingredient is glimepiride.

20. A dosage form according to claim 1, wherein inner portion may optionally contain more than one antidiabetic active ingredients.

21. A pharmaceutical dosage form of a combination of a high dose high solubility active ingredient, in the form of a as modified release formulation and a low dose active ingredient is an antidiabetic drug selected from the group consisting of glibenclamide (glyburide), glipizide, gliclazide, glimepiride, tolazamide, tolbutamide, clorpropamide, gliquidone, nateglinide, mitiglinide,glyburide, glisoxepid, glibornuride, phenbutamide, tolcyclamide, repaglinide, troglitazone ciglitazone, rosiglitizone, pioglitazone, englitazone, acarbose, voglibose, emiglitate, miglitol, farglitazar, (S)-2-ethoxy-3-[4-(2-{4-methanesulfonyloxyphenyl}ethoxy)phenyl]propanoic acid, 3-{4-[2-4-tert-butoxycarbonyl aminophenyl) ethoxy]phenyl}(S)-2-ethoxy propanoic acid and pharmaceutically acceptable salts thereof as an immediate release formulation suitable for swallowing; which comprises an inner portion having a low dose active ingredient as immediate release and an outer portion having a high dose, high solubility active ingredient as modified release, wherein said inner portion is covered by the outer portion from all the sides except a top surface that remains uncovered; wherein said outer portion consists of:
  a) micro matrix particles consisting of a high dose, high solubility active ingredient which is an antidiabetic drug selected from the group consisting of metformin hydrochloride, phenformin and buformin and one or more hydrophobic release controlling agent wherein the weight ratio of high dose, high solubility active ingredient and hydrophobic release controlling agent is in the range of 100:2.5 to 100:30 and
  b) a coating of one or more hydrophoblic release controlling agents on said micro matrix particles), wherein the weight ratio of micromatrix particles and hydrophobic release controlling agent is in the range of 100:2.5 to 100:30.

* * * * *